(12) United States Patent
Perlin

(10) Patent No.: US 8,898,021 B2
(45) Date of Patent: Nov. 25, 2014

(54) METHOD AND SYSTEM FOR DNA MIXTURE ANALYSIS

(76) Inventor: Mark W. Perlin, Pittsburgh, PA (US)

( * ) Notice: Subject to any disclaimer, the term of this patent is extended or adjusted under 35 U.S.C. 154(b) by 0 days.

(21) Appl. No.: 09/776,096

(22) Filed: Feb. 2, 2001

(65) Prior Publication Data

US 2002/0152035 A1 Oct. 17, 2002

(51) Int. Cl.
*G01N 33/48* (2006.01)
*G01N 33/50* (2006.01)
*G01N 31/00* (2006.01)
*G06F 17/15* (2006.01)
*C12Q 1/68* (2006.01)
*G06F 19/18* (2011.01)
*G06F 17/16* (2006.01)
*G06F 17/11* (2006.01)
*G06F 19/22* (2011.01)
*G06F 19/24* (2011.01)

(52) U.S. Cl.
CPC .............. *G06F 19/18* (2013.01); *G06F 17/153* (2013.01); *C12Q 1/6851* (2013.01); *G06F 17/16* (2013.01); *G06F 17/11* (2013.01); *G06F 19/22* (2013.01); *G06F 19/24* (2013.01)
USPC ............. 702/19; 702/20; 702/22; 702/23

(58) Field of Classification Search
USPC ............. 435/6, 91.1, 91.2; 536/23.1, 24.33, 536/23.5, 24.3; 204/461, 466, 612, 616; 382/128, 129, 140; 702/19, 20
See application file for complete search history.

(56) References Cited

U.S. PATENT DOCUMENTS

| | | | |
|---|---|---|---|
| 5,541,067 A * | 7/1996 | Perlin ................................. | 435/6 |
| 5,762,876 A * | 6/1998 | Lincoln et al. .................. | 422/67 |
| 6,274,317 B1 * | 8/2001 | Hiller et al. ....................... | 435/6 |
| 6,750,011 B1 * | 6/2004 | Perlin ............................ | 435/6.11 |
| 6,807,490 B1 * | 10/2004 | Perlin .............................. | 702/20 |

FOREIGN PATENT DOCUMENTS

EP 0812621 A1 * 12/1997

OTHER PUBLICATIONS

Gill et al. (Forensic Science International (1998) 91: 41-53).*
Clayton et al. (Forensic Science International (1998) 91: 55-70).*
Merriam-Webster's Online Dictionary definition of "probability", p. 1 http://www.merriam-webster.com/cgi-bin/dictionary?book=Dictionary&va=probability.*
Abdullah et al. International Journal of Bio-Medical Computing, 1988, vol. 22, pp. 65-72. (abstract only).*
www.dictionary.com definition of genotype, Stedman's Medical Dictionary, 2002.*

(Continued)

*Primary Examiner* — Russell S Negin
(74) *Attorney, Agent, or Firm* — Ansel M. Schwartz

(57) ABSTRACT

The present invention pertains to a process for automatically analyzing mixed DNA samples. Specifically, the process comprises the steps of obtaining a mixed DNA sample; amplifying the DNA sample to produce a product; detecting the product to produce a signal; and analyzing the signal to determine information about the composition of the mixed DNA sample. This DNA mixture analysis is useful for finding criminals and convicting them. This mixture analysis provides high quality estimates, and can determine genotypes, mixture weights, and likelihood ratios. This analysis provides confidence measures in the results it computes, and generates reports and intuitive visualizations. The process automates a tedious manual procedure, thereby reducing the cost, time, and effort involved in DNA forensic analysis. The system can greatly accelerate the rate of DNA crime analysis, and be used to exonerate innocent people.

70 Claims, 8 Drawing Sheets

| | | | Individuals | | |
|---|---|---|---|---|---|
| | | | A | B | C |

| | | | Genotypes G | | |
|---|---|---|---|---|---|
| Alleles | Data d | | 1,2 | 1,3 | 2,3 |
| 1 | 0.75 | | 1 | 1 | 0 |
| 2 | 0.75 | = | 1 | 0 | 1 |
| 3 | 0.50 | | 0 | 1 | 1 |
| | | | 0.50 | 0.25 | 0.25 |
| | | | wA | wB | wC |
| | | | Weights w | | |

(56) References Cited

OTHER PUBLICATIONS

Cao GM. Quantitation of unresolved chromatographic peak using overlapping ratio of profiles of standard chromatographic peaks. Journal of Chromatography A. vol. 746, 1996, pp. 161-167.*

Wietstock SM. DNA composition analysis by nuclease digestion and HPLC. Journal of Chemical Education. vol. 72, 1995, pp. 950-952.*

Wong SC et al. Differential diagnosis of HbEE and Hb E-beta0-Thalassemia by protein and DNA Analyses. Acta Haematologica, 2000, vol. 103, pp. 84-89.*

Definition of variance of a chromatographic peak, www.chromatography-online.org/topics/variance, accessed Jun. 2, 2006.*

Evett et al. Taking account of peak areas when interpreting mixed DNA profiles. Journal of Forensic Science. 1998, vol. 43,, pp. 62-69.*

Foley. Equations for chromatographic peak modeling and calculation of peak area. Analytical Chemistry. 1987, vol. 59, pp. 1984-1987.*

Perlin et al. Toward fully automated genotyping: genotyping microsatellite markers by deconvolution. American Journal of Human Genetics. vol. 57, 1995, pp. 1199-1210.*

Gentalen et al. A novel method for determining linkage between DNA sequences: hybridization to paired probe arrays. Nucleic Acids Research. 1999. vol. 27, pp. 1485-1491.*

Gale et al. Backtracking leukemia to birth: Identification of clonotypic gene fusion sequences in neonatal blood spots. PNAS, 1997, vol. 94, pp. 13950-13954.*

Odell et al. Megakaryocytopoiese in rats with special reference to polyploidy. Blood. 1970, vol. 35, pp. 775-782.*

Perlin et al. Toward fully automated genotyping: Allele assignment, pedigree construction, phase determination, and recombinant detection in Duchenne Muscular Dystrophy. American Journal of Human Genetics, 1994, vol. 55, pp. 777-787.*

Reiss et al. The effect of replication errors on the mismatch analysis of PCR-amplified DNA. Nucleic Acids Research, 1990, vol. 18, pp. 973-978.*

Ballabio et al. PCR test for cystic fibrosis deletion. Nature, 1990, vol. 343, p. 220.*

Merriam-Webster's Online Dictionary definition of "probability," 2004, (one page). Ontained online <<http://www.merriam-webster.com/cgi-bin/dictionary?book=Dictionary&va=probability>>.*

* cited by examiner

|  | | Individuals | | |
|---|---|---|---|---|
|  | | A | B | C |
|  | | Genotypes G | | |
| Alleles | Data d | 1,2 | 1,3 | 2,3 |
| 1 | 0.75 | 1 | 1 | 0 |
| 2 | 0.75 = | 1 | 0 | 1 |
| 3 | 0.50 | 0 | 1 | 1 |
|  | | 0.50 | 0.25 | 0.25 |
|  | | wA | wB | wC |
|  | | Weights w | | |

Figure 1

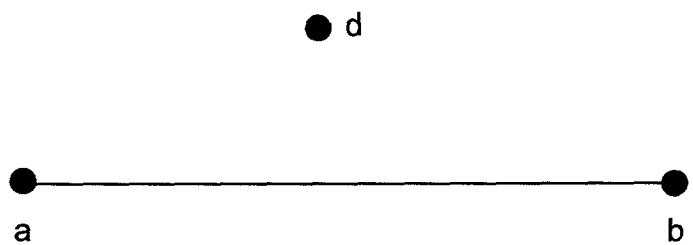
Figure 2.a
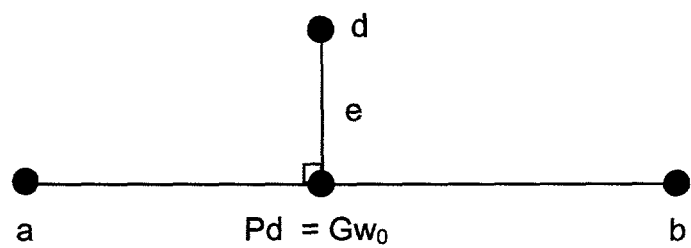
Figure 2.b

Figure 3.a
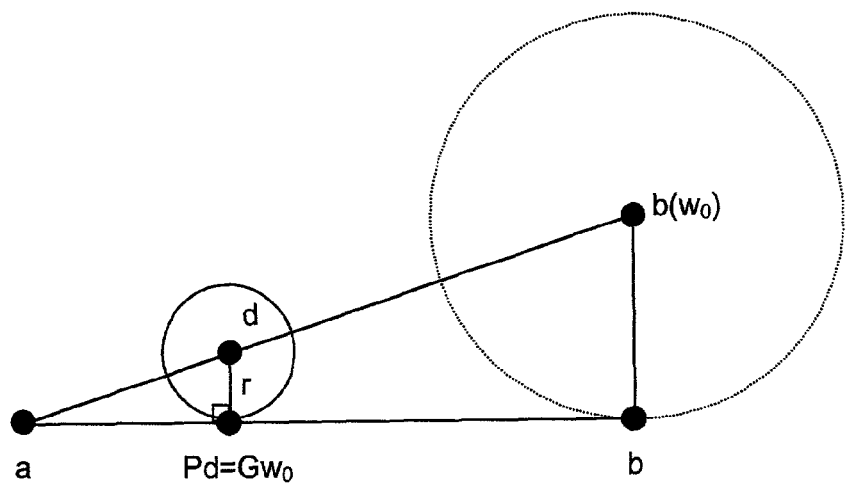
Figure 3.b
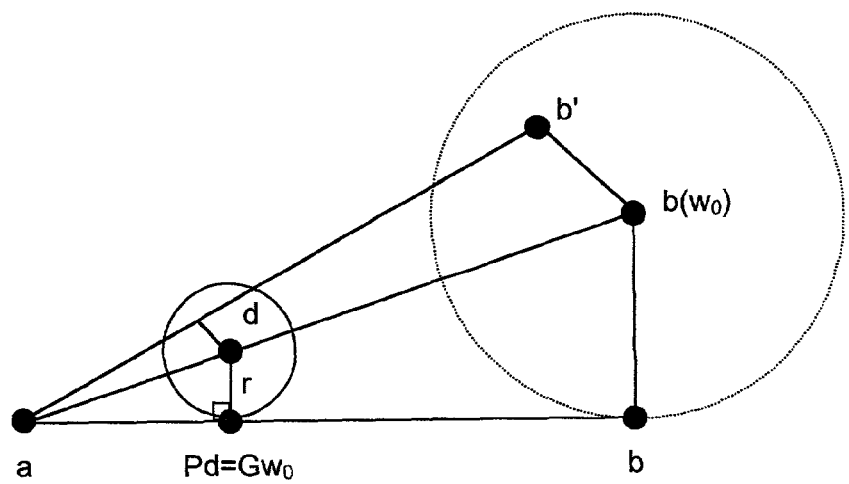

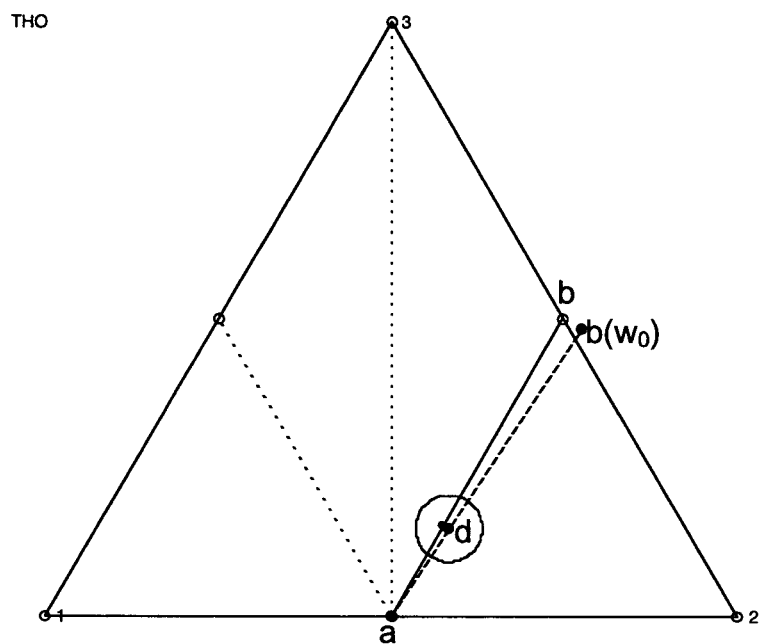
Fig. 4.a
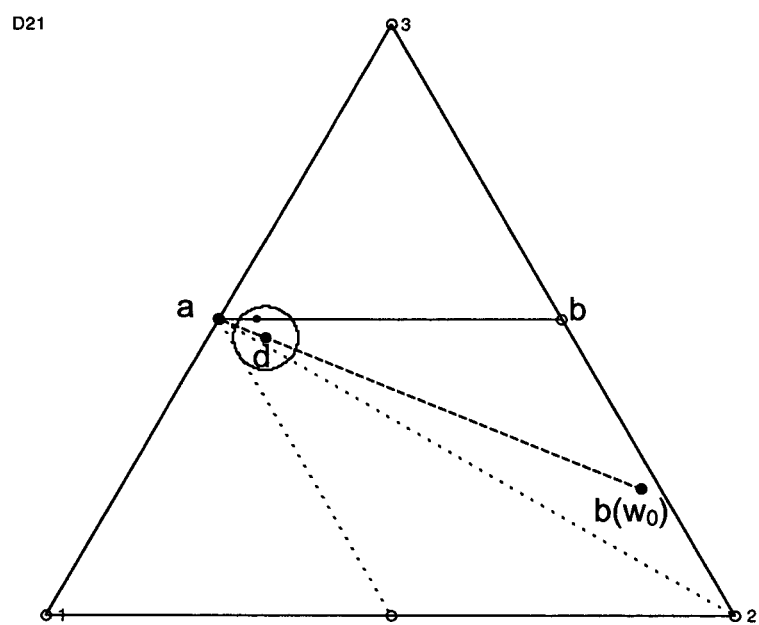
Fig. 4.b

D2

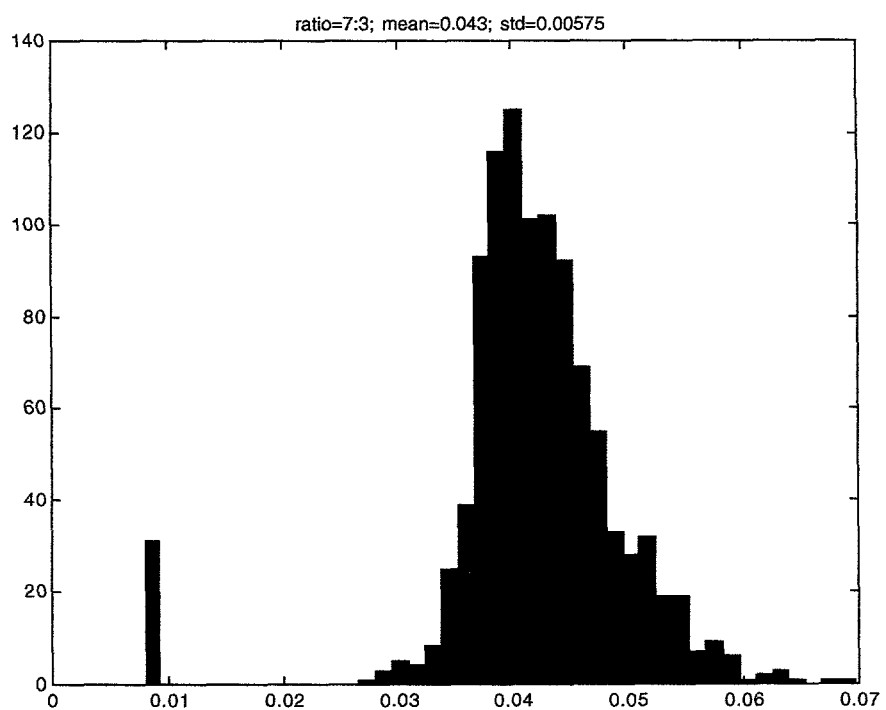
Fig 8.a
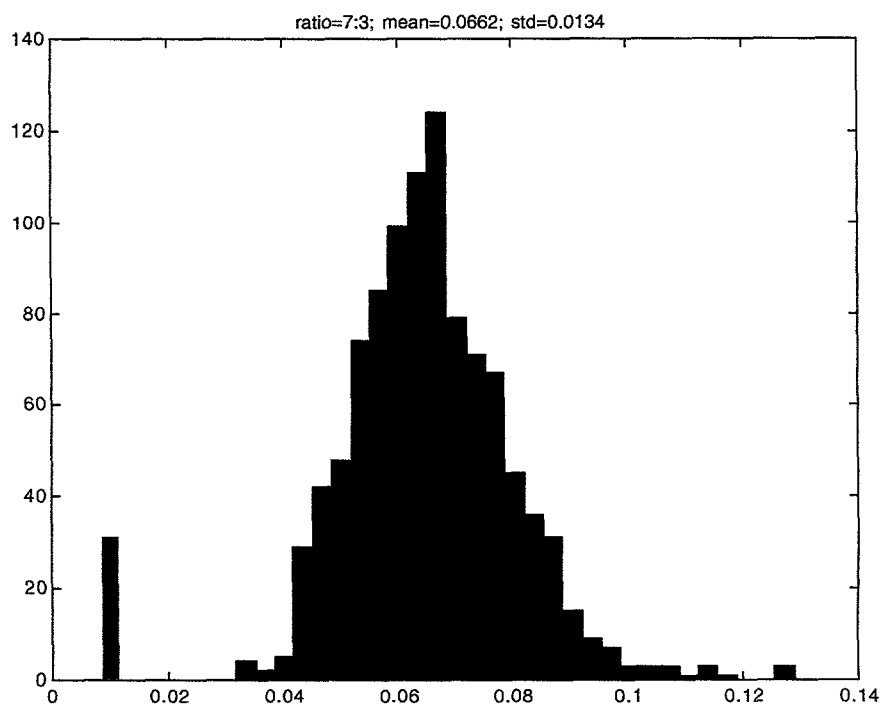
Fig 8.b

METHOD AND SYSTEM FOR DNA MIXTURE ANALYSIS

FIELD OF THE INVENTION

The present invention pertains to a process for analyzing mixtures of DNA molecules. More specifically, the present invention is related to performing experiments that produce quantitative data, and then analyzing these data to characterize a DNA component of the mixture. The invention also pertains to systems related to this DNA mixture information.

BACKGROUND OF THE INVENTION

With the advent of PCR-based STR typing systems, mixed samples can be separated into their individual DNA profiles. Quantitative peak information can help in this analysis. However, despite such advances, forensic mixture analysis still remains a laborious art, with the high cost and effort often precluding timely reporting.

This invention describes a new automated approach to resolving forensic DNA mixtures. This "linear mixture analysis" (LMA) is a straightforward mathematical approach that can integrate all the quantitative PCR data into a single rapid computation. LMA has application to diverse mixture problems. As demonstrated herein on laboratory STR data, LMA can assess the quality and utility of its solutions. Such rapid and robust methods for computer-based analysis of DNA mixtures are helpful in reducing crime.

In forensic science, DNA samples are often derived from more than one individual. In such cases, key objectives include elucidating or confirming a mixed DNA sample's component DNA profiles, and determining the mixture ratios. Current manual qualitative peak analysis of mixed DNA samples is slow, tedious, and expensive. These difficulties can generate considerable delay in the casework analysis of forensic DNA mixtures, underscored by the current USA backlog comprised of over 100,000 unanalyzed rape kits.

Under appropriate data generation conditions, STR peak data can be quantitatively analyzed. Such quantitative approaches have spawned heuristic and computer-based methods that can potentially resolve these complex data. These prior art statistical computer programs are limited in that they typically analyze each STR locus separately, and may require human intervention when combining the locus results into a complete nonoptimized solution (Clayton T M, Whitaker J P, Sparkes R, Gill P. Analysis and interpretation of mixed forensic stains using DNA STR profiling. Forensic Sci. Int. 1998; 91:55-70; Evett I W, Gill P, Lambert J A. Taking account of peak areas when interpreting mixed DNA profiles. J. Forensic Sci. 1998; 43(1):62-69; Gill P, Sparkes R, Pinchin R, Clayton T M, Whitaker J P, Buckleton J. Interpreting simple STR mixtures using allele peak area. Forensic Sci. Int. 1998; 91:41-53), incorporated by reference.

The present invention includes a quantitative analysis method that describes the mixture problem as a linear matrix equation. One name for this novel DNA analysis approach is "Linear Mixture Analysis," or "LMA". Unlike previous methods, the mathematical LMA model uses STR data from all the loci simultaneously for greater robustness. The linear mathematics permits rapid computer calculation, and provides a framework for statistical analysis. An associated error analysis can measure the quality of the overall solution, as well as the utility of each contributing locus.

This specification details the generation of linear mixture data, novel methods of linear mixture analysis, a nonobvious mixture deconvolution technology for determining unknown mixture components, an associated error analysis, the computation of probability distributions, a set of statistical tests, useful bootstrap simulation methods, user interfaces and data visualization for communicating results, utility in forensic applications, and useful extensions of linear mixture analysis.

SUMMARY OF THE INVENTION

The invention pertains to a method of analyzing a mixed DNA sample. The method is comprised of the steps of obtaining a mixed DNA sample. Then there is the step of amplifying the DNA sample to produce a product. Then there is the step of detecting the product to produce a signal. Then there is the step of analyzing the signal to determine information about the composition of the mixed DNA sample.

The invention also pertains to a method for finding suspects. The method is comprised of the steps of obtaining a sample related to a crime wherein the sample includes DNA from a plurality of individuals. Then there is the step of determining mathematically with a computing device a genotype related to an individual in the sample. Then there is the step of comparing the genotype with a database of genotypes to form a comparison. Then there is the step of finding a likely suspect from the database using the comparison.

The invention also pertains to a system for resolving a DNA mixture. The system comprises means for amplifying a DNA mixture, said means producing amplified products. The system further comprises means for detecting the amplified products, said means in communication with the amplified products, and producing signals. The system further comprises means for quantifying the signals that includes a computing device with memory, said means in communication with the signals, and producing DNA length and concentration estimates. The system further comprises means for automatically resolving a DNA mixture into one or more component genotypes, said means in communication with the estimates.

BRIEF DESCRIPTION OF THE DRAWINGS

FIG. 1 shows a representation of information in linear mixture analysis.

FIG. 2(a) shows the relation between a data point and two genotypes. FIG. 2(b) shows a specific perpendicular relationship and point.

FIG. 3(a) shows the closest points to the search space at the minimum solution. FIG. 3(b) shows a contradiction of minimality.

FIG. 4(a) shows a highly confident three allele solution at a locus. FIG. 4(b) shows an ambiguous three allele solution.

FIG. 8(a) shows a distribution from a two unknown mixture problem. FIG. 8(b) shows a distribution from a one unknown mixture problem.

DESCRIPTION OF THE PREFERRED EMBODIMENT

Linear Mixture Data

Figure 5:
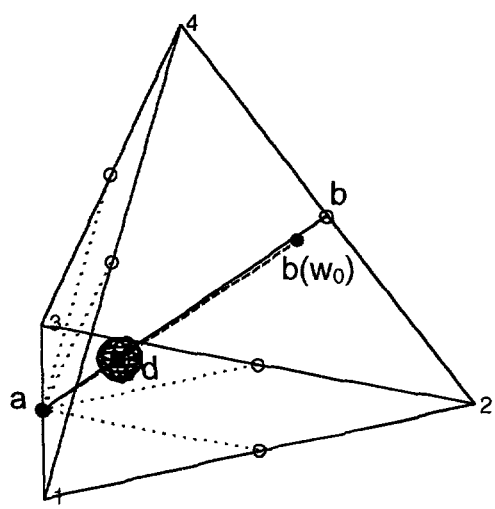
FIG. 5 shows a four allele solution at a locus.

A detailed description of the data generation and initial data analysis process has been given ("Method and System for DNA Analysis," filed Feb. 15, 2000, having Ser. No. 09/504,389), incorporated by reference. This section summarizes the key steps.

Step 1. Sample Extraction. The DNA is extracted from the sample (e.g., a forensic stain). This is preferably done using standard techniques such as cell lysis followed by inorganic solvent extraction, such as phenol chloroform or silica gel membranes. Chelex is another standard extraction mechanism. Additional lysis and processing may be done for extracting sperm DNA. It is preferable to remove PCR inhibitors (e.g., divalent cations, proteins) so that the PCR amplification can proceed as linearly as possible. Additional clean up steps, such as microcon purification, may be helpful. See (Ausubel F M, Brent R, Kingston R E, Moore D D, Seidman J G, Smith J A, et al., editors. Current Protocols in Molecular Biology. New York, N.Y.: John Wiley and Sons, 2001; Dracopoli N J, Haines J L, Korf B R, Morton C C, Seidman C E, Seidman J G, et al., editors. Current Protocols in Human Genetics. New York: John Wiley and Sons, 2001; QIAamp DNA Blood Kit, Qiagen, Valencia, Calif.; Microcon, Millipore, Bedford, Mass.), incorporated by reference.

Step 2. PCR Amplification. The extracted and purified DNA template is then PCR amplified using a preferably multiplexed primer set. It is preferable to quantitate the DNA, and use the amount of DNA template (e.g., 0.5 ng to 2 ng) recommended for use with the multiplex primer set. However, limited sample material or other circumstances may necessitate using smaller or larger DNA amounts (e.g., 1 pg to 1 ug). In such cases, the PCR conditions can be varied. For example, the number of PCR cycles can be increased with very low DNA quantities. With small amounts of DNA (e.g., under 100 pg), SGMPLUS® STR multiplex kit users have increased the cycle number from 28 to 34. It is preferable to use a high quality thermostable polymerase (e.g., AMPLITAQ GOLD® DNA polymerase), along with a hot-start procedure to reduce spurious amplification. See (PROFILERPLUS®STR multiplex kit, COFILER® STR multiplex kit, SGMplus manuals, Applied Biosystems, Foster City, Calif.; POWERPLEX16® STR multiplex kit, Promega, Madison, Wis.; Gill P, Whitaker J, Flaxman C, Brown N, Buckleton J. An investigation of the rigor of interpretation rules for STRs derived from less than 100 pg of DNA. Forensic Sci Intl 2000, 112:17-40), incorporated by reference.

Step 3. Size Separation and Detection. Automated DNA sequencers combine fragment separation and detection. Some older gel-based systems (e.g., Hitachi FM/BIO2® DNA sequencer) perform these operations in separate steps. An adequate quantity and quality of run controls should be used, including internal size standards, allelic ladders, known positive controls, and negative controls. Preferably, the detector (e.g., fluorescent) exhibits a linear response over a large range, and an appropriate amount of PCR product is loaded into the system to work within this linear range, thereby avoiding low signal to noise or saturation of the detector. The detecting step produces data files collected from detected PCR product signals. See (ABI/310® DNA sequencer, ABI/377® DNA sequencer, ABI/3700® DNA sequencer user manuals, Applied Biosystems, Foster City, Calif.; FM/BIO2 user manual, Hitachi Software, South San Francisco, Calif.; MEGABACE® DNA sequencer 1000 user manual, Molecular Dynamics, Sunnyvale, Calif.; SCE/9610® DNA sequencer user manual, SpectruMedix, State College, Pa.), incorporated by reference.

Step 4. Image and Signal Analysis. Baseline removal and color separation are performed on the detected signals. This produces signals in each dye that are not corrupted by peaks from spectrally overlapping dyes. On gel images, lane tracking is performed to identify the one dimensional profiles. On both gel and capillary systems, the internal size standards are tracked, and then used to map pixel location into an estimate of DNA fragment size. The sized signal information is then recorded for further analysis. See (GENESCAN® DNA analysis software user manual, Applied Biosystems, Foster City, Calif.; FM/BIO2 user manual, Hitachi Software, South San Francisco, Calif.; TRUEALLELE®DNA analysis and interpretation software user manual, Cybergenetics, Pittsburgh, Pa.), incorporated by reference.

Step 5. Quantitation and Allelic Analysis. The data signals are compared with the allelic ladder signals; preferably, these signals are in size coordinates. The relevant allelic peaks of each marker are then precisely sized to determine the allele, and possibly other information (e.g., size deviation, allelic designation, genotype). The allelic peaks are quantified to estimate their relative DNA concentration; this can be done using peak height (or area) taken from the signal peak or its modeled function. See (GENOTYPER® DNA interpretation software user manual, Applied Biosystems, Foster City, Calif.; STRCALL® DNA interpretation software user manual, Hitachi Software, South San Francisco, Calif.; TrueAllele user manual, Cybergenetics, Pittsburgh, Pa.; Ng, S.-K., Automating computational molecular genetics: solving the microsatellite genotyping problem, Computer Science Dept, 1998, Carnegie Mellon University), incorporated by reference.

Step 6. PCR Artifact Removal. It is preferable (although not required) to remove PCR amplification artifacts prior to quantitative mixture analysis. PCR stutter can be removed from a locus by calibrating the allele stutter patterns on related samples from a laboratory, and then mathematically removing (or attenuating) the stutter from the examined sample. Relative amplification of alleles within a locus (also termed preferential amplification or heterozygote imbalance) can be adjusted for by calibrating the imbalance on related samples from a laboratory, and then mathematically adjusting allele balance from the examined sample. See (Martens, H. and T. Naes, Multivariate Calibration 1992, New York: John Wiley & Sons 438; Ng, S.-K., Automating computational molecular genetics: solving the microsatellite genotyping problem, in Computer Science. 1998, Carnegie Mellon University; Perlin, M. W., et al., Rapid construction of integrated maps using inner product mapping: YAC coverage of human chromosome 11 Genomics, 1995. 28(2): p. 315-327), incorporated by reference.

The quantified allelic peaks of the PCR amplified sample at a locus behave linearly over a wide range of parameters. Specifically, the relative DNA concentrations at a locus (adjusting for PCR stutter and relative amplification) are proportional to the relative amounts of DNA allele template present. This physical phenomenon is a fact of nature. Poor PCR conditions can induce nonlinear behavior. It is therefore preferable to use optimal DNA template, enzyme, multiplex primers, and other high quality PCR amplification elements.

Linear Mixture Model

Linear Model

In the PCR amplification of a mixture, the amount of each PCR product scales in rough proportion to the relative weighting of each component DNA template. This holds true whether the PCRs are done separately, or combined in a multiplex reaction. Thus, if two DNA samples A and B are in a PCR mixture with relative concentrations weighted as $wA$ and $wB$ ($0 \le wA \le 1$, $0 \le wB \le 1$, $wA+wB=1$), their corresponding signal peaks after detection will generally have peak quantitations (height or area) showing roughly the same proportion. Therefore, by observing the relative peak proportions, one can estimate the DNA mixture weighting. Note that mixture weights and ratios are interchangeable, since the mixture weight $$\frac{[A]}{[A]+[B]}$$

is in one-to-one correspondence with the mixture ratio $$\frac{[A]}{[B]}.$$

To mathematically represent the linear effect of the DNA sample weights (wA, wB, wC, ...), combine all the locus data into a single linear matrix equation:

$$d = G \cdot w + e,$$

which has expected value:

$$d = G \cdot w.$$

Here, column vector d describes the mixture profile's peak quantitation data, matrix G represents the genotypes (column j gives the alleles for individual j), and w is the weight column vector that reflects the relative proportions of template DNA or PCR product. The quantitative data profile d is the product of genotype matrix G and the weight vector w. The more complete data description includes an error term e; while the error term is exploited later on, the expected value form is sufficient for the first parts of the discussion.

More precisely, write the vector/matrix equation $d = G \cdot w$ for mixture coupling (of individuals and loci) as coupled linear equations that include the relevant data:

$$d_{ik} = \sum_j g_{ijk} w_j,$$

where for locus i, individual j, and allele k:
- $d_{ik}$ is the allele k proportion in the observed mixture data at locus i;
- $g_{ijk}$ is the genotype of individual j at locus i in allele k, taking values 0 (no contribution), 1 (heterozygote or hemizygote contribution), or 2 (homozygote contribution), though with anomalous chromosomes other integer values are possible; and
- $w_j$ is the weighting in the mixture of individual j's DNA proportion.

Illustrative Examples

It is useful to motivate the use of vectors and matrices in modeling STR mixtures. This section provides extended illustrative examples.

The first example shows the coupling of DNA mixture weights with relative peak quantities. Suppose that there are three individuals A, B, C represented in a mixture, where 50% of the DNA is derived from individual A, 25% from individual B, and 25% from individual C. Mathematically, this corresponds to a weighting of wA=0.5, wB=0.25, and wC=0.25. Further suppose that at one locus the genotypes are:
- A has allele 1 and allele 2,
- B has allele 1 and allele 3, and
- C has allele 2 and allele 3.

This information, and the predicted peak quantities, are laid out in FIG. 1.

Referring to FIG. 1, the relative data quantity is calculated for each allele at the locus as shown. For example, allele 1's relative data value of 0.75 is calculated from (a) the genotype values of <1, 1, 0> (i.e., the allele is <present, present, absent>) at allele 1 for individuals A, B, and C, and (b) the individuals' DNA mixture weight contributions of <0.50, 0.25, 0.25>. The computation is performed by computing the inner product of these two vectors as (1×0.50)+(1×0.25)+(0×0.25)=0.75.

The information in FIG. 1 can be connected via the linear vector/matrix equation:

$$\begin{bmatrix} \text{alleles} \\ \text{in} \\ \text{mixture} \end{bmatrix} = \begin{bmatrix} \begin{bmatrix} \text{alleles} \\ \text{of} \\ A \end{bmatrix} \begin{bmatrix} \text{alleles} \\ \text{of} \\ B \end{bmatrix} \begin{bmatrix} \text{alleles} \\ \text{of} \\ C \end{bmatrix} \end{bmatrix} \cdot \begin{bmatrix} wA \\ wB \\ wC \end{bmatrix}$$

Representing each allele as a position in a column vector, this forms the linear relationship:

$$\begin{bmatrix} 0.75 \\ 0.75 \\ 0.50 \end{bmatrix} = \begin{bmatrix} \begin{bmatrix} 1 \\ 1 \\ 0 \end{bmatrix} \begin{bmatrix} 1 \\ 0 \\ 1 \end{bmatrix} \begin{bmatrix} 0 \\ 1 \\ 1 \end{bmatrix} \end{bmatrix} \cdot \begin{bmatrix} 0.50 \\ 0.25 \\ 0.25 \end{bmatrix}$$

which is the mathematical expression of Table 1. Note that the sum of alleles in each allele column vector (whether mixture or individual) is normalized to equal two, the number of alleles present.

With multiple loci, the weight vector w is identical across all the loci, since that is the underlying chemical mixture in the DNA template. This coupling of loci can be represented in the linear equations by extending the column vectors d and G with more allele information for additional loci.

To illustrate this coupling of DNA mixture weights across multiple loci, next add a second locus to the three individual mixture above. At locus two, suppose that the genotypes are:
- A has allele 1 and allele 2,
- B has allele 2 and allele 3, and
- C has allele 3 and allele 4.

Combine this vector information via the partitioned matrix equation:

$$\begin{bmatrix} locus1 \\ \text{mixture} \\ \text{alleles} \\ \text{----} \\ locus2 \\ \text{mixture} \\ \text{alleles} \end{bmatrix} = \begin{bmatrix} \begin{bmatrix} locus1 \\ A's \\ \text{alleles} \end{bmatrix} \begin{bmatrix} locus1 \\ B's \\ \text{alleles} \end{bmatrix} \begin{bmatrix} locus1 \\ C's \\ \text{alleles} \end{bmatrix} \\ \text{---} \quad \text{---} \quad \text{---} \\ \begin{bmatrix} locus2 \\ A's \\ \text{alleles} \end{bmatrix} \begin{bmatrix} locus2 \\ B's \\ \text{alleles} \end{bmatrix} \begin{bmatrix} locus2 \\ C's \\ \text{alleles} \end{bmatrix} \end{bmatrix} \cdot \begin{bmatrix} wA \\ wB \\ wC \end{bmatrix}$$

Representing each allele as a position in a column vector:

$$\begin{bmatrix} 0.75 \\ 0.75 \\ 0.50 \\ -- \\ 0.50 \\ 0.75 \\ 0.50 \\ 0.25 \end{bmatrix} = \begin{bmatrix} \begin{bmatrix} 1 \\ 1 \\ 0 \\ - \\ 1 \\ 1 \\ 0 \\ 0 \end{bmatrix} \begin{bmatrix} 1 \\ 0 \\ 1 \\ - \\ 0 \\ 1 \\ 1 \\ 0 \end{bmatrix} \begin{bmatrix} 0 \\ 1 \\ 1 \\ - \\ 0 \\ 0 \\ 1 \\ 1 \end{bmatrix} \end{bmatrix} \cdot \begin{bmatrix} 0.50 \\ 0.25 \\ 0.25 \end{bmatrix}$$

Multiple loci produce more data and provide greater confidence in estimates computed from these linear equations.

Problem Formulations

Given partial information about equation d=G·w, other elements can be computed by solving the equation. Cases include:

When G and w are both known, then the data profile d can be predicted. This is useful in search algorithms.

When G and d are both known, then the weights w can be computed. This is useful in confirming a suspected mixture, and in search algorithms.

When d is known, inferences can be made about G and w, depending on the prior information available (such as partial knowledge of G). This is useful in human identification applications.

The DNA mixture is resolved in different ways, depending on the case.

In the preferred embodiment, normalize the mixture profile data vector d at each locus. That is, for each locus, let NumAlleles be the number of alleles found in an individual's genotype (typically NumAlleles=2, one for each chromosome). For each allele element of the locus quantitation data, multiply by NumAlleles, and divide by the sum (over the observed alleles) of all the quantitation values for that locus. Then, the sum of the normalized locus quantitation data is NumAlleles, which totals 2 in the illustrative example above.

Linear Mixture Analysis

A fundamental problem in DNA mixture analysis is determining the mixture weights (also termed proportions or ratios). This section focuses on the problem of how to compute the mixture weights, given the mixture data d, and the genotype vectors of the J known contributors.

Resolving DNA mixtures using LMA entails (a) obtaining DNA profile data that include a mixed sample, (b) representing the data in a linear equation, (c) deriving a solution from the linear equation, and (d) resolving the DNA mixture from the solution. The LMA approach is illustrated in the following problem formulations.

Geometric Perspective

The geometry of the linear model is usefully represented by the relations of the genotype vectors in multidimensional data space. The genotypes are points that may be usefully defined as either the pure allele ($\{0, 1, 2\}$ valued) vectors, or as the continuous real-valued data points generated by the PCR process (which may contain PCR stutter, relative amplification, and other artifacts). This geometric model can be used with any number of component genotypes, and with any number of loci. The basis vectors of this space are the relevant alleles, and points in the space describe multiplex PCR measurements (preferably renormalized within each locus). A vector coordinate is the renormalized peak quantity (e.g., height, area) corresponding to a relative estimate of DNA concentration for one allele.

In a "mixture combination", the real-valued nonnegative elements of the weighting vector w sum to 1. That is, the points of w form a simplex. Define the space of all possible genotype mixtures C(G) as the J−1 dimensional subspace of $R^K$ (K the number of alleles considered) generated by all mixture combinations G·w of the weighted columns of G. For J different individuals, the elements of w lie in the J−1 dimensional simplex, so C(G) (with full G rank) is a J−1 dimensional subspace.

With J=2 contributors to the mixture, J−1 equals 1. Then, the three points (component genotypes a and b, and mixture data d) lie on a plane, and can be easily visualized (FIG. 2.a). The solution subspace G·w=[a b]·w of possible mixtures in this case is a line. This line describes all physically realizable linear mixtures of genotypes a and b, where the exact location is given by the mixture combination weight w.

The least squared error solution to d=G·w+e minimizes the length of the error vector e. The minimum solution e connects data point d to its perpendicular projection on the line formed by a and b (FIG. 2.b). This projection of d onto the subspace C(G) generated by mixture combinations of the columns of G (i.e., [a b]·w, for positive w summing to 1) can be computed via the perpendicular projection operator P:

$$P = G \cdot (G^T \cdot G)^{-1} \cdot G^T$$

Applying operator P to d produces the point Pd, the least squares estimate $G \cdot w_0$. This projection can be generalized to account for known covariance structure. Perpendicular projection operators and least squares estimation are described in (Christensen, R., Plane Answers to Complex Questions: A Theory of Linear Models 1996, New York: Springer-Verlag), incorporated by reference.

Determining Mixture Weights

Consider the case where all the genotypes G and the mixture data d are known, and the mixture weights w need to be determined. This problem is resolved by solving the linear equations d=G·w+e for w using a least squares matrix division method. One standard method is linear regression (Seber GAF. Linear Regression Analysis. New York: John Wiley & Sons; 1977), incorporated by reference. Such computer implementations often use singular value decomposition (SVD) (Press W H, Teukolsky S A, Vetterling W T, Flannery B P. Numerical Recipes in C: The Art of Scientific Computing. Second ed. Cambridge: Cambridge University Press; 1992), incorporated by reference.

In the MATLAB® numerical analysis and visualization software programming language, w can be estimated as:

$$w = G \backslash d$$

using the built-in matrix division operation "\". With full rank matrices, matrix multiplication via the normal equations computes the weights as:

$$w = (G^T \cdot G)^{-1} \cdot G^T \cdot d.$$

A preferred embodiment for robustly determining the weight wA is using the projection operator Pd to set the ratio to ||Pd−b||/||a−b||. This embodiment applies the constraint that the weight factors sum to unity.

Others have computed mixture weights by minimizing parameters at single loci (Gill P, Sparkes R, Pinchin R, Clayton T M, Whitaker J P, Buckleton J. Interpreting simple STR mixtures using allele peak area. Forensic Sci. Int. 1998; 91:41-53). In the LMA model, this early work can be reinterpreted as minimizing at a single locus the sum of squares deviation $\|d - G \cdot w\|^2$ over w for each feasible integer-valued genotype matrix G. This prior art has a limited single-locus view of the data, which restricts the amount of derivable useful information; there is no known way to combine the separate single locus partial solutions into one global optimum. Moreover, such prior art does not make special use of the known reference genotypes, which contain much valuable information. LMA improves on such earlier mixture methods by providing a mathematical basis that can use the data from all the loci simultaneously in a rapid optimized numerically computed global minimization. Moreover, LMA permits the genotype matrix entries to assume any possible value, and not just integers.

Analogous mixture problems occur outside molecular biology, and are similarly modeled using linear matrix equations. In chemometrics, the approach is termed "multivariate calibration" (MC) (Martens H, Naes T. Multivariate Calibration. New York: John Wiley & Sons; 1992), incorporated by reference. These MC methods are quite different than computing genotypes (and mixture weights) from the data. For example:

(1) MC finds real-valued solutions but genotypes are whole numbers. MC finds solutions in a real-valued multidimensional Euclidean function space $R^K$. However, genotype solutions lie in a subset of the integer-valued lattice in $R^K$.

(2) Calibration exploits signal continuity whereas locus patterns contribute combinatorially. MC inversion methods exploit the continuity of close solutions. However, the genotype mixture problem instead has combinatorial solutions, since each locus contributes its own subsets of integer-constrained possibilities (i.e., allele combinations).

(3) MC methods rely on multiple samplings whereas (with limited forensic samples) mixture data typically arise from a single multiplex PCR experiment. MC typically uses multiple data objects (i.e., five or more spectra), and finds mixture solutions via linear operators (e.g., inverse matrices). In this forensic STR mixture problem, usually only a single data object (the DNA-limited multiplex PCR) is obtained, and different search algorithms are required.

Therefore, novel methods are needed that are specifically tailored to the requirements of the STR mixture genotype data, as described next.

Mixture Deconvolution

Crime scene stains are typically comprised of J contributors, where J−1 are of known genotype, and 1 genotype is unknown. For example, with J=2, in the mixture data d, the victim's genotype a is known, but the perpetrator's genotype b is unknown. This is often the case in sexual assault cases. If this unknown genotype b were determined, it could be used to match a specific suspect, or to search a DNA database of likely suspects (e.g., convicted offenders) for a matching profile. Such a (relatively) unique b would greatly improve upon the current art, in which a large set of non-unique candidate suspect genotypes is generated.

Yet this problem is hard, and is as yet unsolved in the prior art. The reason for this is that the quantitative allele measurements for the K alleles create a vast K-dimensional search space. For example, with just J=2 individuals, K ranges from about 50 to 100 dimensions for modern 10 to 15 locus multiplex STR experiments, assuming no stutter removal (and about half that dimension when stutter is removed). K increases with marker panel size (e.g., with currently anticipated STR, SNP and other genetic markers), as well as with the number J of contributing individuals. Even when J−1 contributors are known, the unknown $J^{th}$ contributor can assume any one of a combinatorial number of genotypes drawn from possible allele values in each of the K dimensions. For example, even restricting the possible alleles to the three values $\{0, 1, 2\}$, the number of solutions is $3^{100}$, a rather large number which is approximately $10^{48}$, or one trillion trillion trillion trillion possibilities.

Interestingly, there is a highly novel, useful, and nonobvious problem reduction. Given J−1 known contributors, the search space can be reduced to a small, finite J−1 dimensional simplex. For example, with a two person (one known, one unknown) mixture, the problem reduces to searching for a minimum on a line segment (i.e., a small bounded continuous one dimensional interval). This search can be done in under 0.1 seconds using standard minimization procedures on an inexpensive personal computer. The prior art is limited to vast combinatorial searches of discrete genotype possibilities that are intractable on even the most powerful computers. The current invention improves on this by changing the problem to a far simpler search on a just few (i.e., J−1) bounded continuos parameters; the genotype vectors are found incidently during the process. Unintuitively, the invention makes efficient use of increasing quantities of data to improve the accuracy and confidence of the genotype estimate.

This section describes the "mixture deconvolution" invention. Given the quantitative mixture data d, and J−1 known contributing genotypes, the unknown contributor genotype b is automatically, accurately, and efficiently computed.

Consider the case of J individuals, where J−1 of the J genotypes are known, the quantitative mixture data profile d is available, and the task is to find the unknown genotype b along with the mixture weighting w. This important problem is currently unsolved in the prior art. The invention's solution is demonstrated here.

Determining Genotype Profiles

Consider first the special case where the mixture weights w known, and J=2. That is, there are two individuals A and B, one of the two genotypes (say, a) is known, the other individual's genotype (say, b) is not known, the mixture weighting w is known, and the quantitative mixture data profile d is available.

Expand $d = G \cdot w + e$ in this case as:

$$d = wA \cdot a + wB \cdot b + e,$$

where a and b are the genotype column vectors of individuals A and B, and wA and wB=(1−wA) are their mixture weights. Then, to resolve the genotype, algebraically rewrite this equation as:

$$b = (d - wA \cdot b - e)/wB$$

or, equivalently, as:

$$b(wA) = (d - wA \cdot gA)/(1 - wA) - e/(1 - wA)$$

and, taking expected values, obtain:

$$b(wA) = (d - wA \cdot gA)/(1 - wA)$$

and then solve for b by vector arithmetic. The computed b(wA) is the normalized difference of the mixture profile minus a fraction of A's genotype. The accuracy of the solution increases with the number of loci used, and the quality of the quantitative data. Typically, however, the mixture weights w are not known.

Consider next the case where the mixture weights w are not known, with J=2, genotype a is known, but genotype b is not known. The goal is to make inferences about the genotype matrix G starting from a mixture data profile d. This case has practical applications for forensic science. In one typical scenario, a stain from a crime scene may contain a DNA mixture from the victim and an unknown individual, the victim's DNA is available, and the investigator would like to connect the unknown individual's DNA profile with a candidate perpetrator. This scenario typically occurs in rape cases. The perpetrator may be a specific suspect, or the investigator may wish to check the unknown individual's DNA profile against a DNA database of possible candidates. If the mixture weight wA were known, then the genotype b could be computed immediately from the vector difference operation (with known weights) just described.

Minimization Algorithm

Since wA is not known, one workable approach is to search for the best weight w in the [0,1] interval that satisfies additional constraints on the problem. By setting wA equal to this best w, this computes the genotype g(wA) as a function of this optimized wA value, and derives b=g(wA). A suitable constraint is the prior knowledge of the form that possible solution genotype vectors g can take. It is known that solutions must have a valid genotype subvector at each locus (e.g., having alleles taking on values 0, 1 or 2, and summing to 2). One may also consider null alleles, corresponding to failed (or low copy number) PCR amplifications. This knowledge can be translated into a heuristic function of b(w) which evaluates each candidate genotype solution b against this criterion. The result of this "mixture deconvolution" algorithm is a computed genotype b and the mixture weights w.

The heuristic applied is a function of the unknown weight w, the observed data profile d, and the known genotype a. Since d and a are fixed for any given problem, in this case the function depends only on the optimization variable w. For any given w in (0,1), compute the vector:

$$b(w)=(d-w \cdot a)/(1-w).$$

Note that $$b=b(w)+e/(1-w),$$

so that $$e=(1-w)(b-b(w)).$$

To minimize the error $\|e\|^2$, it suffices to minimize the expression:

$$(1-w)^2|b-b(w)|^2.$$

The primary issue is how to select the minimum distance to the correct genotype b at each value of w, so that it can be compared with vector b(w).

Compute and record the deviation $dev_{locus}(e(w))$ as follows. The $dev_{locus}$ function at one locus is defined as:

Assume the genotype comprises one homozgotic allele. Compute the deviation by finding the index of the largest peak, and forming a vector oneallele that has the value 2 at this index and is 0 elsewhere. Let dev1 be the sum of squares difference between genotypes b(w) and oneallele.

Assume the genotype comprises two heterozygotic alleles. Compute the deviation by finding the index of the two largest peaks, and forming a vector twoallele that has the value 1 at each of these two indices and is 0 elsewhere. Let dev2 be the sum of squares difference between genotypes b(w) and twoallele.

Return the lesser of the two deviations as the genotype difference, adjusted by the (1−w) scaling for the error term: $(1-w)^2 \min(dev1, dev2)$.

To compute dev(e(w)), sum the component $dev_{locus}(e(w))$ at each locus. That is, the heuristic function is the scalar value $$dev(e(w)) = \sum_{loci} dev_{locus}(e(w)).$$

Minimize this function over w in [0,1] to find wA, and estimate b from the computed b(wA). If desired, the summation terms can be normalized to reflect alternative weightings of the loci or alleles, e.g., based on variance. Other heuristic functions can be used that reflect reasonable constraints on the genotype vectors (Gill P, Sparkes R, Pinchin R, Clayton T M, Whitaker J P, Buckleton J. Interpreting simple STR mixtures using allele peak area. Forensic Sci. Int. 1998;91:41-53), incorporated by reference.

To assess the quality of the computed STR profile, use information from this minimization search. Rule checking can identify potentially anomalous allele calls, particularly when peak quantities or sizes do not conform to expectations (Perlin M. Computer automation of STR scoring for forensic databases. In: First International Conference on Forensic Human Identification in The Millennium; 1999; London, UK: The Forensic Science Service; 1999), incorporated by reference. Quality measures can be computed on the genotypes, which may suggest problematic calls even when no rule has fired. A most useful quality score in this mixture analysis is the deviation dev(e) of the computed genotype. Low deviations indicate a good result, whereas high scores suggest a poor result. It may be helpful to partition the deviations by locus, using the locus deviation function $dev_{locus}(e)$. When a locus has an unusually high deviation, it can be removed from the profile, and the resulting partial profile then used for human identity matching.

J Individuals, 1 Unknown

With J>2 individuals and 1 unknown genotype, the data can similarly be resolved. With J=2 the mixture space (of weights or mixed genotypes) is parameterized by a one dimensional line. In general, with arbitrary individuals J the mixture space is parameterized by a J−1 dimensional simplex.

The search is conducted over the J−1 dimensional simplex for weights $w_1, \ldots, w_{J-1}$. That is, to define the J-vector w, J−1 weights are selected so that $w_1+\ldots+w_J=1$, and $0 \leq w_j \leq 1$, for all j. The continuos genotype approximation points explored in the image of the J−1 dimensional simplex weights are:

$$b(w)=(d-w_1 \cdot a_1 - \ldots -w_{J-1} \cdot a_{J-1})/(1-w_1-\ldots-w_{J-1}),$$

where $(d-w_1 a_1 - \ldots w_{J-1} \cdot a_{J-1})$ can be written in matrix form as:

$$d-[a_1 \ldots a_{J-1}] \cdot [w_1 \ldots w_{J-1}]'.$$

Genotype b is the closest valid genotype to b(w), chosen by the fast $dev_{locus}(e(w))$ functions defined above. With $w_J$ defined as:

$$w_J=(1-w_1-\ldots-w_{J-1}),$$

the error vector e(w) is then:

$$e(w)=w_J(b-b(w)),$$

so the squared error is computed as:

$$\|e\|^2 = w_J^2 \cdot |b-b(w)|^2$$

One result of the search is the minimizing mixture weight $w_0$. Another is the least squared error vector $e(w_0)$ that extends from data point d into its perpendicular projection Pd. Point Pd resides within the genotype mixture subspace C(G) (the image under G of the simplex mixture weights), and is the closest point to d that lies in that subspace. The search also returns b, the closest valid genotype to $b(w_0)$. The definition of a "valid" genotype depends on the nature of the DNA template and the PCR experiment.

Minimization Method

The minimization over the simplex can be performed using most practical global search algorithms. In the neighborhood of the correct solution, the search space has parabolic shape. This suggests using a search algorithm that can exploit this feature. While virtually any robust search procedure will successfully implement the required function minimization, a straightforward algorithm is described.

Step 1. (Global) Parameterize the J−1 dimensional simplex as a J−1 dimensional unit cube, since $w_J$ is just $(1-w_1 \ldots w_{J-1})$. Perform a global minimization by preferably partitioning the J−1 cube into n parts (e.g., n=2 to 1000, depending on the search space) along each dimension, and then forming the $n^{J-1}$ volume elements as the product space of the 1−D partitions. The partitioning can depend on the anticipated value of w. Compute the squared error function $\|e\|^2 = w_J^2 \cdot |b - b(w)|^2$ at a point within each voxel. Record the set of smallest values and their points.

Step 2. (Local) Choose either Step 2a or Step 2b. Continue the search at the local level.

Step 2a. (Local iterative) Repeat the procedure at voxel sample points that appear to be potential minima, but focus in on smaller volumes around the point.

Step 2b. (Local search) Use a standard minimization algorithm. For one dimensional search, use golden section search, inverse parabolic interpolation, or Brent's method. In higher dimensions, use a general methods such as Nelder-Mead simplex search, or direction set search. There are many good local search algorithms that work here (Forsythe, G. E., M. E. Malcolm, and C. B. Moler, Computer Methods for Mathematical Computations 1977, Englewood Cliffs, N.J.: Prentice-Hall; Brent, Richard P, 1973, Algorithms for Minimization without Derivatives, Prentice Hall, Englewood Cliffs, N.J.; Press, W. H., et al., Numerical Recipes in C: The Art of Scientific Computing. Second ed 1992, Cambridge: Cambridge University Press), incorporated by reference.

Correctness of Minimization

The mixture deconvolution method starts with mixture data from J individuals, and the known genotypes of J−1 individuals. The method determines the best estimate of the $J^{th}$ genotype, along with the J mixing weights. In evaluating the possible weighting values w, the method estimates b(w) and finds the closest b to this estimate.

Many different b's may be considered as the weights w vary during this process. However, there is no orthogonality constraint (between b(w) and the C(G) subspace, with b a column of G) on such closest candidate genotypes. Therefore, is not obvious that the correct b is ever chosen: might there be some b' that is closer than the correct b to $b(w_0)$? With an incorrect genotype b' cloaking the true b, the error would not be minimized and the correct weight $w_0$ and genotype estimates $b(w_0)$ and b would not be found.

Background: Referring to geometry FIG. 3.a, there exists a genotype point b in $R^K$, such that the simplicial subspace C([a b]) is the closest subspace to d out of all possible C([a $b_i$]) choices. Let G=[a b], and $G_i$=[a $b_i$]. For J=2, C(G) is the finite line segment connecting points a and b; this line segment represents all possible error-free mixtures of genotypes a and b. The perpendicular projection point $P_G d = G w_0$ is the closest mixture point to d in C(G), or indeed in any mixture space $C(G_i)$. The distance $r = |(I-P)d|$ between points d and Pd is the minimal distance between d and any point in any $C(G_i)$.

Assertion: At point $b(w_0)$, the minimization search method finds the genotype b corresponding to the minimal distance r.

Proof: Referring to FIG. 3.b, suppose that there exists a b' that is closer to $b(w_0)$ than is b. Then the angle dab' is less than angle dab. Hence the line C([a b']) intersects the circle centered at d of radius r. Therefore there exists a mixture in C([a b']) whose distance to d is less than r. But this violates the minimality assumption for r, and the assertion is proved. Note that sin θ provides a bijection between minimal angles and minimal distances. QED.

To extend the proof for arbitrary J, note that there exists a minimal r such that for some genotype matrix G=[$a_1$ $a_2$ $a_{J-1}$ b], the perpendicular projection operator $P_G d$ is closest to data point d. The J points {$a_1$ $a_2$ ... $a_{J-1}$ b} form a J−1 dimensional simplex which is orthogonal to the error vector $e(w_0) = (P_G - I)d$ of length r. As with the J=2 case, there is a J−1 dimensional sphere centered at d of radius r, and another centered at $b(w_0)$ of radius $r/w_J$. By a minimality argument of lines, distances, and angles similar to one presented for the J=2 case, but using the interior of the spheres instead those of the circles, there can exist no b' closer than b to $b(w_0)$. Therefore, regardless of the number of contributors J, the minimum weights $w_0$ and genotype vector b are found via the $b(w_0)$ search of the simplex domain.

Error Analysis

Variances are calculated from the linear model d=G·w+e, together with the global minimal solution $Pd = Gw_0$. Note that the error vector e can be computed as (I−P)d. The variances can be computed from the data using standard linear regression methods (Christensen, R., Plane Answers to Complex Questions: A Theory of Linear Models 1996, New York: Springer-Verlag; Martens, H. and T. Naes, Multivariate Calibration. 1992, New York: John Wiley & Sons 438; Seber, G. A. F., Linear Regression Analysis 1977, New York: John Wiley & Sons), incorporated by reference. When genotype vectors are computed from the data, as in mixture deconvolution, the computed genotypes can be usefully viewed as parameters of the model, than as fixed components of the design matrix G.

Estimating the variance $\sigma_d^2$ of the data d. With K allele measurements, and J individuals, G is a K×J design matrix (of rank J), and E[d]=G·w. Assuming (for now) equal variances in each component of the observed quantitative data, the dispersion of the data is given by $D[d] = \sigma^2 I_K$. Then an unbiased estimate of the variance $\sigma_d^2$ is the sample variance $S^2$:

$$S^2 = \frac{\|d - G \cdot w_0\|^2}{dof} = \frac{\|e(w_0)\|^2}{dof} = \frac{RSS}{dof}$$

where RSS is the "residual sum of squares", and dof is the "degrees of freedom". Typically in linear modeling, dof=K−J. However, in some cases, the degrees of freedom are adjusted, depending the actual number of parameters used in the estimation. For example, in mixture deconvolution, when the J−1 weights are varied, the $J^{th}$ weight is computed from the others. Hence the dof in this case is K−J+1. Bootstrap algorithms often dispense with these distinctions altogether, particularly in variance calculations, and just use K. In practice, with the values of K used in multiplex PCR (e.g., 25 to 50), small differences in the dof will not greatly affect the statistical computations.

Estimating the variance $\sigma_w^2$ of the mixture weights w. The dispersion of the weighting vector w is $D[w_0] = \sigma_d^2 (G' \cdot G)^{-1}$. Since $w_0$ is estimate with the smallest variance, estimate the weight variances as:

$$S^2 \cdot (G' \cdot G)^{-1}$$

The variance of the $i^{th}$ weight is $S^2$ times the $i^{th}$ diagonal entry $(G' \cdot G)^{-1}_{ii}$. (Covariances between the weights are described by the off-diagonal entries.) In particular, this estimate has utility for assessing the quality of the mixture problem, since a small variance $\sigma_w^2$ (e.g., $S^2 \cdot (G' \cdot G)^{-1}_{11}$) in the mixture weight $w_0$ indicates a high confidence in the solution (e.g., $w_0$ and b, with mixture deconvolution).

Estimating the variance $\sigma_b^2$ of the genotype estimate b(w). Since d=G·w+e, $$b(w) - b = e/w_J$$

and so $\sigma_b^2$ is proportional to $\sigma_d^2/w_J$. Therefore, a reasonable estimate of $\sigma_b^2$ at the solution point is $S^2/w_J$.

When there is additional information about the covariance structure of the observations, one can use the general covariance matrix V. Important special cases include $V = \sigma^2 I$ (used above), and V a diagonal matrix with $v_{ii} = \sigma_i^2$ (weighted least squares). The covariance matrix V is readily estimated from the data when multiple mixture experiments are performed on the DNA samples. One need only use the standard statistical definition $$V_{ij}=cov(X_i,Y_j)=E[(X_i-EX_i)(Y_j-EY_j)],$$

where X and Y are vectors of random variables corresponding to quantitative allele measurements obtained from multiplex PCR experiments.

A highly useful effect of the invention is that variances and standard deviations can be computed directly from the experimental data in order to quantify a confidence in the results. The most preferred embodiment derives the estimates described here (including mixture weights, genotype vectors, and variances) using a linear model of the data. By applying least squares estimation (or, equivalently, maximum likelihood estimation), exact distributions are not required. An alternative preferred embodiment obtains variance estimates and confidence intervals using standard bootstrap simulation procedures (Efron, B. and R. J. Tibshirani, An Introduction to the Bootstrap 1993, New York: Chapman & Hall), incorporated by reference. These simulation methods, however, can provide useful extensions for solving additional DNA mixture problems, as described next.

Bootstrap Methods

A more difficult mixed DNA problem is that of two unknown contributors. That is, there are J contributors, J−2 with known genotype, and 2 genotype profiles unknown. For example, with J=3, in the mixture data d, the victim's genotype a is known, but there are two unknown genotypes $b_1$ and $b_2$, one of which (at least) is the perpetrator. This can happen, for example, in a sexual assault when there are (a) multiple assailants, or (b) a consensual partner and an assailant. If the unknown genotypes $b_1$ and $b_2$ were determined, they could be used to match specific suspects, or for searching a DNA database of likely suspects (e.g., convicted offenders) for a matching profile. Such (relatively) unique $b_1$ and $b_2$ would greatly improve upon the current art, in which a large set of candidate suspect genotypes is generated.

This problem (more than one unknown contributor) is quite hard, and not feasibly solved in the prior art. Within the vast K-dimensional search space of quantitative allele measurements, two genotype profiles are to be ascertained. With J=2 individuals, and K=100, how can the genotypes possibly be separated and uniquely identified? For with three feasible allelic values, each person can have one of $10^{50}$ possibilities, and in combination, the number of possibilities is the square of that figure: $10^{100}$, or a "google" of possible genotype solutions. Brute force computation is clearly not a viable approach.

However, with a novel combination of mathematics, computation, and information, the described invention can usefully solve this problem. In a nonobvious way, the invention combines the method detailed above for deriving one unknown (and its confidence) from a mixed DNA profile, together with DNA database information. Since the goal is to match a suspect in the database of candidate offenders (which includes all available profiles from actual suspects in the case, as well as all other accessible DNA databases), the genotype of the unknown individual is preferably included in the matchable database in order for a match to actually occur.

It is useful to have a null distribution of scores for a population of randomly selected candidate solutions. Then, a candidate solution can be compared with this null distribution, and a decision made about the whether or not the score suggests a likely candidate. This section describes how to construct such null distributions using statistical simulation resampling via bootstrap methods (Efron, B. and R. J. Tibshirani, An Introduction to the Bootstrap 1993, New York: Chapman & Hall), incorporated by reference. It further describes how to use confidence scores generated by the invention together with such null distributions.

Two Unknown Case

A method for resolving two unknown DNA profiles using a DNA database proceeds as follows.

The first step constructs and characterizes the null distribution of randomly constructed solution confidence scores. With two unknowns, this is done by simulating one unknown, and then using mixture deconvolution to compute the second unknown, along with an error estimate (e.g., the variance) of the solution. A function of this error estimate is used as a confidence score.

Step 1a. Gather data.

Analyze the DNA mixture peaks to determine the useful loci.
  A locus that is useful for mixture analysis typically has more than one allele present.
Determine the relevant alleles within each useful locus. The relevant alleles should preferably have a relative DNA concentration that exceeds some preset or data-dependent threshold.
When feasible, retrieve the population frequencies within each locus of the relevant alleles. If the prior allele distributions are not available, then preferably use uniformly distributed frequencies.

Step 1b. Sample a distribution of genotypes $\{g_i\}$ for the population that represents the mixture alleles. In the preferred embodiment, this is done by simulating a large number (e.g., 100 to 5,000 generally suffice, with 500 to 2,000 the most preferred range) of genotypes. Preferably, use the prior locus allele frequency distribution (restricted to alleles found in the mixture) to sample genotypes representative of the population that could have generated the mixture.

Step 1c. Compute a distribution of confidence scores for the mixture data allele population. In the J−2 known mixture case, genotypes a and b are the two unknowns. For each sampled genotype $g_i$, set genotype a to $g_i$. Use the mixture deconvolution method to estimate the weight vector $w_0$, the genotype b, and a confidence score in the solution based on the error. Preferably, the confidence score $s_i$ is a function of the estimated variance in d ($\sigma_d^2$) or $w_0$ ($\sigma_w^2$). Record the set of confidence scores $\{s_i\}$.

Step 1d. Compute parameters (e.g., mean, variance, confidence interval) of the distribution of sampled confidence scores $\{s_i\}$. Continuing with the bootstrap procedure, these simulated distribution parameters are computed by the "plug-in" principle for bootstrap statistics (e.g., averages, moments, order statistics, or any computable function).

Step 1e. Use the computed parameters of $\{s_i\}$ to help identify outliers of unusually high quality. In the most preferred embodiment, this is done by modeling the $\{s_i\}$ distribution (e.g., as a normal, beta, or gamma function), and determining tail probabilities based on the value of the confidence score. Alternatively, confidence intervals can be constructed by the bootstrap for identifying outlier confidence scores. In any case, the bootstrap mean and standard deviation can provide an approximate guide to identifying noncentral values.

A second computation is then performed. For every candidate genotype $h_i$ in the database of possible offenders, a mixture deconvolution is performed, and a confidence score is computed. These scores are then compared with the null distribution of confidence scores from Step 1 to identify any genotypes $h_i$ of unusually high confidence that match the data. The set of such highly confident genotypes, preferably in ranked order, is then returned. More specifically, iterating over the candidate genotypes $\{h_i\}$ in the database:

Step 2a. Select a candidate $h_i$ from the database. The database comprises the available suspect, convicted offender, or other known genotypes.

Step 2b. Perform mixture deconvolution. Set $a=h_i$, and compute b. Compute the error measures of the mixture deconvolution solution, as described above.

Step 2c. Compute the confidence score $t_i$ for $h_i$ using an error-based scoring function commensurable with the one used in Step 1c above. Note that:
When the null distribution has a modeled probability function, the tail probability can be used.
The actual $S^2$ value of $h_i$ is a useful numerical score, since smaller values suggest higher confidence. These quadratic values can follow a $\chi^2$ distribution. Moreover, ratios of sample variances can follow an F distribution, which can provide additional ranking and hypothesis testing information.

Step 2d. Compare the confidence score with the null distribution. Compare $t_i$ with the null distribution $\{s_i\}$.

Step 2e. Identify the possible matching genotypes. If $t_i$ is a high confidence score for candidate $h_i$, then record the genotype (preferably along with its score) as $(h_i, t_i)$ for further evaluation. When bootstrapped confidence intervals are used, note that the endpoints provide a straightforward decision rule for identifying outliers. The ranked outliers of high confidences are recorded for further examination.

The result of this procedure is a set of ranked genotypes $\{h_i\}$ that are in the suspect database which match the mixture data unusually well. In practice, this set will generally be either empty (no matches were found), a singleton (only one good match was found), or a doubleton (both DNA contributors reside in the database). This null distribution comparison method uses a database of DNA profiles that provide a set of candidate first individuals. It further uses a mixture deconvolution method that can complete a J–1 mixture problem and compute a second individual, along with its confidence score.

The advantages of this method are many; several are enumerated. The mathematical analysis is fully automatable on a computing device, so that the current large amount of human forensic expert effort is not required. The method can solve complex problems that even human experts cannot handle, and thereby identify candidate suspects. The results provide statistical confidence measures for reporting useful to the prosecution or the defense. By reducing large lists of candidate to just a few (or even no) suspects, a vast amount of police investigative work is entirely eliminated. This elimination can save tens of thousands of dollars in even one case, and can help better apply limited law enforcement resources to reducing crime.

One Unknown Case

It can be useful to obtain additional measures of confidence in a genotype solution (e.g., when using mixture deconvolution). A variation of the bootstrapped null distribution method above can be used to obtain useful confidence information when there are J–1 known contributor profiles, and one unknown contributor profile.

Step 1. Form the null distribution. This works similarly to the case above. However, here there are J–1 known genotypes, and so these are fixed throughout. Only the one unknown profile is sampled.

Step 1a. Gather data. Determine the alleles in the mixture data. Use uniformly distributed frequencies when population estimates are not available. Note that multiple estimates can be computed, one for each population allele frequency distribution.

Step 1b. Sample a distribution of genotypes $\{b_i\}$ for the population that represents the mixture alleles. In the most preferred embodiment, all the alleles in the mixture at a locus are used. This approach is in keeping with current reporting practice. In an alternative preferred embodiment, it may be possible to use a subset of such alleles. For example, in a three locus case with J=2, suppose that locus d has alleles $\{1, 2, 3\}$, and reference profile a has alleles $\{1,2\}$; then it logically follows that the unknown genotype b must include allele $\{3\}$ at that locus, and so the allele combination $\{1,2\}$ would not be possible for b at that locus. While this embodiment is more efficient than including all possible alleles, it can be less robust with quantitative data, particularly when the DNA quantity of the allele is relatively small.

Step 1c. Compute a distribution of confidence scores for the mixture data allele population. In the J–1 known mixture case, genotype b is the only unknown. For each sampled genotype $g_i$, set genotype b to $g_i$. Use linear modeling error estimation such as perpendicular projection to estimate the weight vector $w_0$, and a confidence score $s_i$ as above in the solution based on the error. This geometrical calculation is simpler (and faster) than searching for unknown genotypes. Record the set of confidence scores $\{s_i\}$.

Step 1d. Compute parameters (e.g., mean, variance, confidence interval) of the distribution of sampled confidence scores $\{s_i\}$. Use the "plug-in" principle for bootstrap statistics.

Step 1e. Use the computed parameters of $\{s_i\}$ to help identify outliers of unusually high quality. In the most preferred embodiment, model the $\{s_i\}$ distribution (e.g., as a normal, beta, or gamma function), allowing the determination of tail probabilities based on the value of a confidence score. Alternatively, use confidence intervals.

Step 2. Compare with the null distribution. This works similarly to the case above. However, here there are J–1 known genotypes, and the single unknown genotype is computed using mixture deconvolution. Thus, there is just one score (that of the mixture deconvolution solution) to compare against the null distribution.

Step 2a. Compute the genotype b from the data. This is preferably done using the mixture deconvolution invention.

Step 2b. Determine the error measures of the mixture deconvolution solution.

Step 2c. Compute the confidence score t for b using the error-based scoring function used in Step 1c above.

Step 2d. Compare the confidence score with the null distribution. Compare t with the null distribution $\{s_i\}$.

Step 2e. Ascertain whether or not b is a high confidence matching genotype. This is done using the results of Step 2d.

Zero Unknown Case

In the case of J knowns, the minimum variance can be determined directly by least squares projection of the data d vector into the J–1 simplex subspace of mixed genotype vectors. However, bootstrap resampling provides another mechanism for assessing the error, hence the quality of the solution. This can be useful when the data deviates greatly from linear behavior. Simulations for error distribution estimation have been well described, including both bootstrapping pairs and bootstrapping residuals (Efron, B. and R. J. Tibshirani, An Introduction to the Bootstrap 1993, New York: Chapman & Hall), incorporated by reference.

Probability Distributions

It is useful to compute probabilities from the observed data. This can be done once the data or error distributions are modeled. It is reasonable to assume normal distributions for the experimental error in PCR amplification, electrophorectic band migration, and fluorescent detection. These assumptions lead to a normal error model for the observed DNA quantities. In an alternative preferred embodiment, the error distribution is modeled directly from the data of many identical mixture experiment replications; this empirical error model is then used in place of the theoretical normal model.

Data Distribution

Assume that the error vector components $e_i$ are normally distributed. Then $e \sim N_K(0, \sigma^2 I_K)$, and hence $d \sim N_K(G \cdot w, \sigma^2 I_K)$, where K is the number of alleles included in the quantitative analysis, and G is a K×J genotype matrix. That is, the probability of the data d is approximated by the multivariate normal distribution:

$$P\{d \mid G, w\} = \frac{1}{(2\pi\hat{\sigma}^2)^{\frac{K}{2}}} \exp\left[-\frac{\|G \cdot w - d\|^2}{2\hat{\sigma}^2}\right]$$

where $\hat{\sigma}^2$ is the sample variance estimate computed from $S^2$. This probability attains its maximum value when G is correct, and $w_0$ is the least squares estimate.

It is also known that $$\frac{RSS}{\sigma^2} = \frac{dof \cdot S^2}{\sigma^2} \sim \chi^2_{dof}$$

which characterizes the sample variance as having a chi-squared distribution.

Suppose that the error is unbiased $E(e)=0$, but its dispersion is more generally $D[e]=\sigma^2 V$, rather than the uniform $\sigma^2 I_K$. With this covariance structure, the residual sum of squares is:

$$f' \cdot f = (G \cdot w - d)' V^{-1} (G \cdot w - d)$$

hence the probability distribution is:

$$P\{d \mid G, w\} = \frac{1}{(2\pi)^{\frac{K}{2}} |V|^{\frac{1}{2}}} \exp\left[-\frac{(G \cdot w - d)' V^{-1} (G \cdot w - d)}{2\hat{\sigma}^2}\right]$$

Weight Distribution

The distribution of the mixture weight vector w can be directly computed using the mathematics of linear models (Seber, G. A. F., Linear Regression Analysis 1977, New York: John Wiley & Sons), incorporated by reference. Given the variance $\hat{\sigma}^2$, one immediately has:

$$\sigma_w^2 = \sigma_d^2 (G' \cdot G)^{-1}$$

Therefore, the distribution of the weights is $w_0 \sim N_J(w, \sigma_w^2)$ and the distribution of the weight variation as $(w_0 - w)' G'G (w_0 - w)' \sim \chi_J^2$. When the error covariance structure is a known constant matrix $\sigma^2 V$, the dispersion of w generalizes to:

$$\sigma_w^2 = \sigma_d^2 (G' \cdot V^{-1} \cdot G)^{-1}$$

These distributions permit the comparison of different mixture weights, the assessment of relative likelihood, and the determination of confidence intervals. Moreover, the variance estimate $\hat{\sigma}_w^2$ (or the standard deviation) is a highly useful measure of the confidence in the obtained results.

Genotype Distribution

For comparing (or ranking) likely genotypes from the data, it is useful to have a numerical score. One powerful and well-accepted score is the likelihood ratio (Edwards, A. W. F., Likelihood, Expanded ed. 1992 Baltimore: Johns Hopkins University), incorporated by reference. To compare the hypothesis of one genotype $b_1$ relative to another one $b_2$, one can form the likelihood ratio (LR):

$$LR(d) = \frac{Pr\{d \mid H_2\}}{Pr\{d \mid H_1\}} = \frac{Pr\{d \mid a, b_2\}}{Pr\{d \mid a, b_1\}}$$

The value of the LR provides a measure of belief in one hypothesis over another. The detailed computation of the LR (for any number of individuals J) via its component probabilities is described below.

An LR may include hypotheses concerning "unknown" genotypes. Note that the mixture deconvolution method permits ascertainment of a genotype (with high confidence), given the other J−1 genotypes in the mixture. Using associated variance and probability estimates, this ascertainment suggests that a very high probability is associated with the correct "unknown", whereas very low probabilities are associated the incorrect "unknowns". That is, the supposedly "unknown" may actually be quite known from the data. These probabilities are useful in weighting the possibilities based on the data, as shown next.

For conviction in court, it would be useful to present a statistical measure that describes the degree of confidence in the defendant's genotype based on the data. Given the distribution of the data under different models, one can determine the posterior probability of the genotypes. For example, consider the representative likelihood ratio:

$$LR(d) = \frac{Pr\{d \mid H_p\}}{Pr\{d \mid H_d\}} = \frac{Pr\{d \mid a, b\}}{Pr\{d \mid a, *\}},$$

evaluated at the observed data vector d. This LR compares the prosecution's hypothesis that the quantitative mixture data d are generated by victim a and the defendant b, relative to the defense hypothesis that the data are generated by the victim a and an unknown random person. Similar derivations and alternative formulations have been described (Evett, I. W. and B. S. Weir, Interpreting DNA Evidence: Statistical Genetics for Forensic Scientists 1998, Sunderland, Mass.: Sinauer Assoc; Evett, I. W., P. Gill, and J. A. Lambert, Taking account of peak areas when interpreting mixed DNA profiles. J. Forensic Sci., 1998 43(1): p. 62-69), incorporated by reference.

If the defendant's genotype is $b_1$, then the LR becomes:

$$LR(d) = \frac{Pr\{d \mid a, b_1\}}{\sum_{genotype\ i} Pr\{d \mid a, b_i\} \cdot Pr\{b_i\}}$$

The prior genotype probabilities $Pr\{b_i\}$ can be computed (with or without $F_{st}$ correction) from population allele frequency information in the usual way (Balding, D. J. and R. A. Nichols, DNA profile match calculation: how to allow for population stratification, relatedness, database selection and single bands, Forensic Sci Int, 1994, 64: p. 125-140; Evett, I. W. and B. S. Weir, Interpreting DNA Evidence: Statistical Genetics for Forensic Scientists, 1998, Sunderland, Mass.: Sinauer Assoc), incorporated by reference. The other probability to evaluate is $$Pr\{d \mid a, b_i\},$$

the probability of the observed mixture data d, given the two component genotypes. This term is needed for computing both the numerator and denominator.

The determination of Pr{d|a,b$_i$} does not appear in the prior art of DNA mixture analysis. Indeed, it is desperately needed, but conspicuously absent, in a seminal mixture analysis paper (equation 5, Evett, I. W., P. Gill, and J. A. Lambert, Taking account of peak areas when interpreting mixed DNA profiles. J. Forensic Sci. 1998, 43(1): p. 62-69). However, by using the linear modeling invention, these probabilities can be estimated using the probability estimates already described.

In a first preferred embodiment, Pr{d|a,b} is computed at a point at a closest location. For J=2 individuals, this sets G=[a b]. In general, for Pr{d|G}, the procedure is to construct the perpendicular projection operator $P_G = G(G'G)^{-1}G'$, and find the error vector $e = (I-P_G)d = (d - Gw_1)$ that projects d onto the closest point $P_G d = Gw_1$ in the J−1 dimensional simplex C(G). The squared error e'e then equals the term that appears in the exponent of the probability:

$$P\{d \mid G\} \cong P\{d \mid G, w_1\} = \frac{1}{(2\pi\hat{\sigma}^2)^{\frac{K}{2}}} \exp\left[-\frac{\|G \cdot w_1 - d\|^2}{2\hat{\sigma}^2}\right]$$

Since the length of the error |e| is minimized at the point $Gw_1$, the normal function is maximized there, and this can be a reasonable estimate, particularly with small variances. This distribution partitions the genotype measurement space into nested cones that radiate out from the data point d.

In a second, more preferred embodiment, Pr{d|a,b} is computed more accurately by considering all possible mixture weights. This is done (with J=2) by integrating over all possible values of the mixture weight w:

$$Pr\{d|a,b\} = \int_0^1 Pr\{d|a,b,w\} \cdot Pr\{w\} dw$$

When integrating over a likelihood ratio LR(d), the w integration can be performed separately for each term, or, preferably, taken over the entire LR. For general genotypes G having J individuals, the mixture weight vector w lies within the J−1 unit simplex, and the integral is taken over the entire simplex:

$$Pr\{d \mid G\} = \int_{w \in simplex(J-1)} Pr\{d \mid G, w\} \cdot Pr\{w\} \cdot dw$$

In this decomposition, the first probability function Pr{d|G,w} is estimated as:

$$P\{d \mid G, w\} = \frac{1}{(2\pi\hat{\sigma}^2)^{\frac{K}{2}}} \exp\left[-\frac{\|G \cdot w - d\|^2}{2\hat{\sigma}^2}\right]$$

In the most preferred embodiment, the variance estimate $\hat{\sigma}^2$ is set by the globally minimal variance. In an alternative embodiment, the variance used is scaled according to the hypothesis, so that $\hat{\sigma}^2$ depends on the $S^2$ of the genotype under consideration.

The second function Pr{w} is the probability of the mixture weight vector w, prior to having seen the data d. In one preferred embodiment, a uniform prior can be used, with all mixture weight vectors having equal probability. In a second most preferred embodiment, the prior is computed from the mixture weights observed (or sampled) from a relevant population of cases. This can be done by using the invention's linear mixture model, possibly together with mixture deconvolution, and accurately determining the mixture weights, hence the prior Pr{w} for the crime stain population. With small variances, the mass of the integral will be tightly centered around the minimization point $Gw_1$ in the simplex C(G), and the form of the prior may have little effect on the computed probability. In the art of empirical Bayesian estimation, beta distributions and other "unknown" priors are successfully employed (Carlin, B. P. and T. A. Louis, Bayes and Empirical Bayes Methods for Data Analysis, 2000, Chapman & Hall/CRC Press), incorporated by reference.

The third function dw is the differential of the integration. This will cancel out in a likelihood ratio calculation, and therefore does not affect most calculations.

This ability to compute the LR $$LR(d) = \frac{Pr\{d \mid a, b_1\}}{\sum_{genotype\ i} Pr\{d \mid a, b_i\} \cdot Pr\{b_i\}}$$

by appropriately weighting the prior probabilities Pr{b$_i$} based on the weight of evidence in the data Pr{d|a,b$_i$} represents a strikingly useful advance over the prior art. Current forensic reporting practice typically uses full weighting of all possible genotypes in a mixture (National Research Council, Evaluation of Forensic DNA Evidence: Update on Evaluating DNA Evidence, 1996, Washington, D.C.: National Academy Press), incorporated by reference. At each locus, then, the full weight of each possible genotype is currently used, instead of the weight as determined by the data. Examining the effect on the denominator is shown by:

$$\sum_{genotype\ i} Pr\{d \mid a, b_i\} \cdot Pr\{b_i\} \underset{(1)}{\cong} Pr\{b_1\} \underset{(2)}{\ll} \sum_{genotype\ i} Pr\{b_i\}$$

Relationship (1) expresses the fact that, in general, the probability Pr{d|a,b$_1$} of the correct genotype b, has an exponentially greater likelihood than the probability Pr{d|a,b$_i$} of any of the other genotypes b$_{i \neq 1}$. Thus, the only term that is typically apparent in the data weighted sum over the genotypes is Pr{b$_1$}.

Relationship (2) is the observation that the probability of just one of the possible genotypes is less than the sum of the probabilities across all possible genotypes. In a two person mixed sample, a three allele locus (and, for that matter, a four allele locus) has six possible genotype contributors. So considering all six possibilities, instead of just one, will reduce that loci's multiplicative contribution to the LR by a roughly factor of 6.

Taken over all 13 CODIS loci, the multiplication of independent locus LRs would reduce the total LR by a factor of about $6^{13}$, or over $10^{10}$ (i.e., ten billion) fold. That is, by not properly weighting the true chance of a "random man" given the data, the prosecution can incorrectly concede to the defense an astronomical amount of likelihood. This concession can become most crucial when poor DNA samples from crime scenes reduce the power of the STR data (fewer loci, PCR artifacts, allelic dropout, etc.).

The LR calculations above made use of the multiplicative combination rule for independent LRs (Edwards, A. W. F., Likelihood, 1992, Baltimore: Johns Hopkins University; Lindgren, B. W., Statistical Theory. Fourth ed. 1993, New York, N.Y.: Chapman & Hall), incorporated by reference. For multiple independent loci, this is written as:

$$LR(d) = \frac{Pr\{d|H_2\}}{Pr\{d|H_1\}} = \prod_{locus\ i} \frac{Pr\{d_i|H_2\}}{Pr\{d_i|H_1\}} = \prod_{locus\ i} LR_i(d_i)$$

Thus, the likelihoods (or probabilities) of the data and genotypes can be determined separately at each locus, and then combined later on. This permits focusing on the properties of single loci, with the knowledge that the single locus results can easily be combined to compute a composite result.

An LR for any number J of contributors can be computed using LMA. This is because LMA provides the key enabling factor: the probability function $Pr\{d|G,w\}$ of the data d given any hypothesis about the genotype G and weight w parameters. The geometrical computations of LMA permit an estimate of the variance, whether by normal theory or bootstrap resampling. One can specify the hypothesis of the prosecution $H_p$ regarding known genotypes $G_{p,known}$ and unknown genotypes $G_{p,unknown}$, and the hypothesis of the defense $H_p$ regarding the alternative known genotypes $G_{d,known}$ and unknown genotypes genotypes $G_{d,unknown}$. There may be constraints relating common genotype parameters in $G_{p,known}$ and in $G_{d,unknown}$. After forming the likelihood ratio, sum over all possibile genotype configurations (restricted for efficiency to the alleles found in the mixture data) over all the unknown genotype variables in ($G_{p,known} \cup G_{d,unknown}$), and simultaneously integrate out the mixture weights w lying in the J−1 dimensional simplex of feasible mixture weights. For computational efficiency, it may be useful to structure the problem with a hierarchical (or empirical) Bayes model, and use Markov Chain Monte Carlo (MCMC) methods for more rapid integration (Berger, J. O., Statistical Decision Theory and Bayesian Analysis. Second ed 1985, New York: Springer Verlag; Tanner, M. A., Tools for Statistical Inference: Methods for the Exploration of Posterior Distributions and Likelihood Functions 1996, New York: Springer Verlag), incorporated by reference.

Computer Methods

There are various computer methods that are useful in implementing LMA and mixture deconvolution. The use of numerical methods (integration, minimization, search, etc.), matrix algebra, multivariate regression, efficient algorithms, and statistical calculations are described elsewhere in this specification. Many of these operations are built directly into high level mathematical programming languages such as MATLAB and S-plus.

Simulation is a powerful computational method. In population genetics, many problems can be solved numerically by resampling from simulated genotypes. To do this, one needs a genotype simulator. In the preferred embodiment, genotypes are simulated at each locus independently. For a given set of possible alleles (based, for example, on the alleles appearing in the mixture data) and their population frequencies, alleles are sampled using a random number generator and a decision function based on the cumulative distribution of the allele frequencies. The effect of population inbreeding is accounted for by using corrected allele frequencies that include $F_{st}$.

Visualization is a highly effective mechanism for rapidly exchanging information with a user. Novel visualizations of geometric genotype relationships are described in this specification, both for the complete genotype, as well as for individual loci. To render a three allele mixture system, it is best (when feasible) to focus on the two dimensional simplex image of the measurement space, which uses the constraint that the weights sum to 1. The geometric graphics computation can be done in three dimensions, and then projected onto the two dimensional surface (triangle) for user display by means of a linear transformation such as the 2×3 matrix:

| −0.70711 | 0.70711 | 0 |
| −0.40825 | −0.40825 | 0.8165 |

Examples of such automatically rendered visualizations are shown for a three allele locus in FIGS. 4.a and 4.b.

For rendering visualizations in four allele dimensions, it is preferable to perform geometric graphics computation in the natural 4-D space, and then project onto the three dimensional region (tetrahedron) for user display by means of a linear transformation such as the 3×4 matrix:

| −0.70711 | 0.70711 | 0 | 0 |
| −0.40825 | −0.40825 | 0.8165 | 0 |
| −0.28868 | −0.28868 | −0.28868 | 0.86603 |

Using computer software that includes a three dimensional renderer (e.g., the plot3 function in MATLAB) can then flexibly project the image into the 2-D for user interaction. An example of such an automatically rendered visualization for a four allele locus is shown in FIG. 5.

Figure 6:
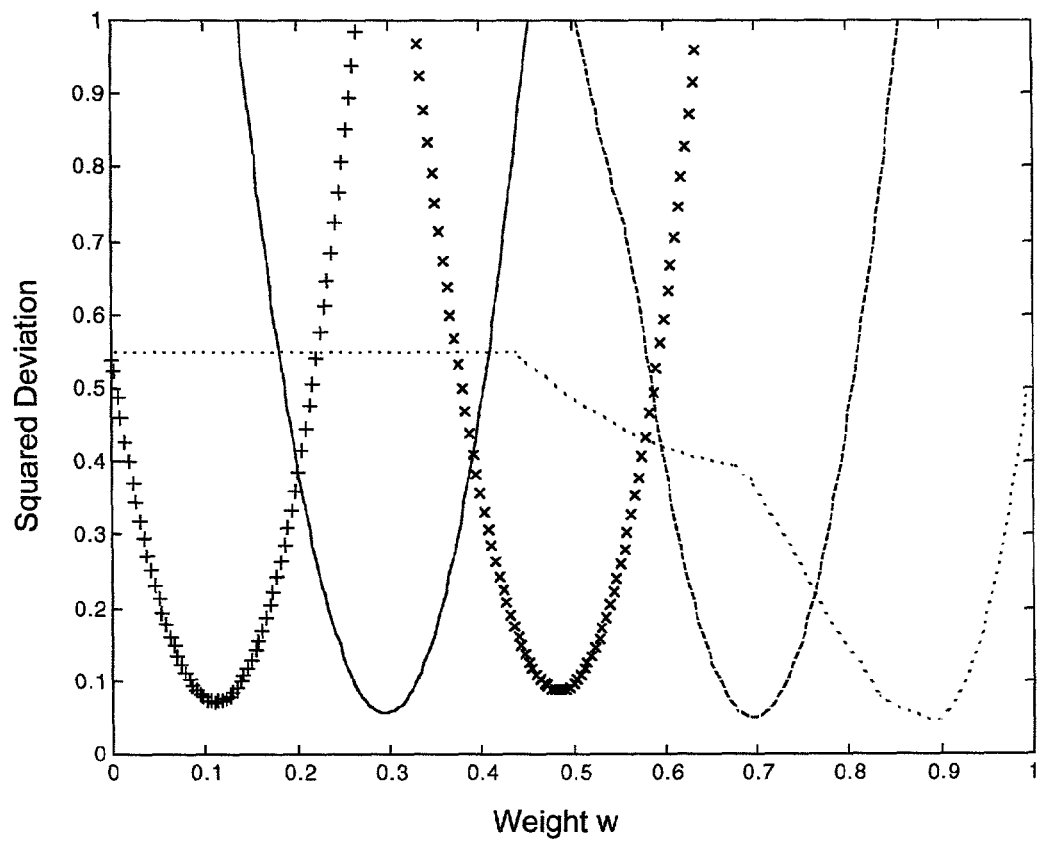
FIG. 6 shows minimization curves for different mixing weights.
Figure 7:
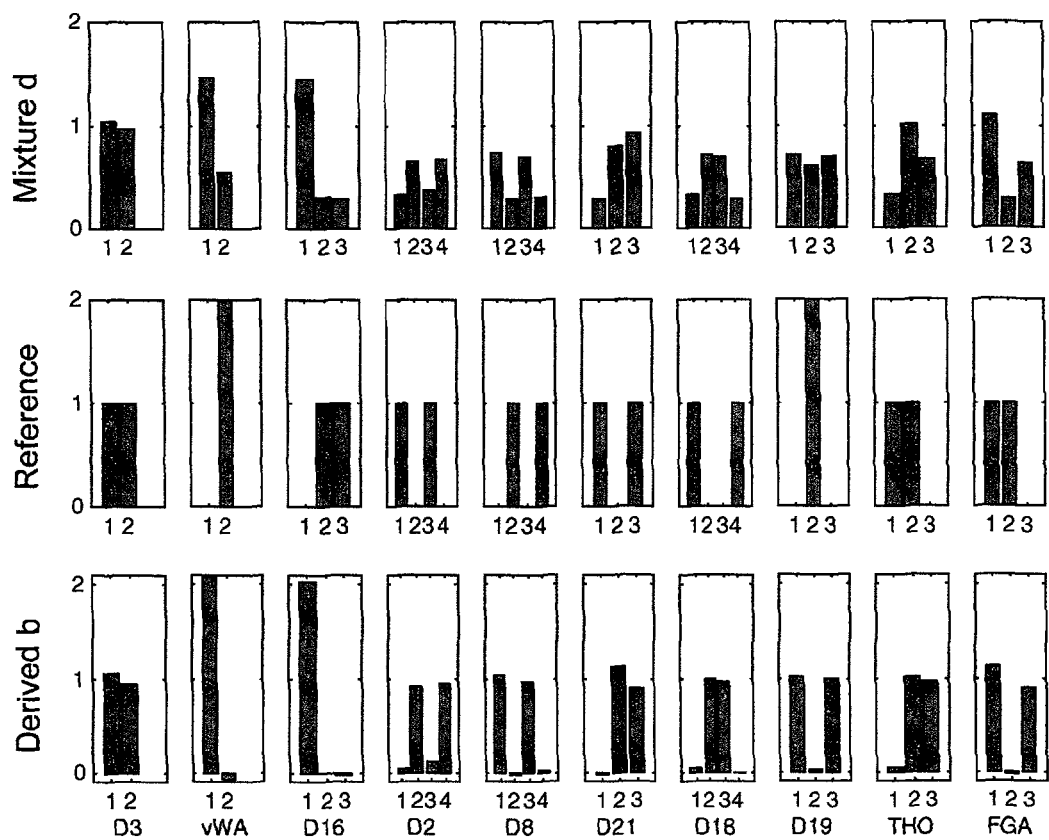
FIG. 7 shows a mixture deconvolution solution.

To understand the behavior and reliability of LMA search methods, it is useful to present the associated minimization curve. An automatically rendered visualization for a minimization curve is shown in FIG. 6. To see the data and its analysis in terms of quantified peaks, it is useful to view the genotypes and mixture results in a way that focuses on the relevant alleles at each locus. An automatically rendered visualization for genotypes and mixture results is shown in FIG. 7. The user can interact with these two visualizations (e.g., a mouse device controlling a slider). Adjusting the weight will change both the location on the minimization curve (or higher dimensional surface), as well as change the calculated mixture heights in the genotype figure. This interactive feature makes visually apparent how a calculated mixture resembles a valid genotype only when near a correct mixture weight.

Data Results

Methods described above are shown via examples on a mixture data set.

Data Generation

Two anonymous human DNA samples (A and B) were analyzed both individually, and in different mixture proportions (10:90, 30:70, 50:50, 70:30, 90:10). PCR amplification was performed on the samples on a PCT-100 thermocycler (MJ Research, Waltham, Mass.) using the ten STR locus SGMplus multi-mix panel (PE BioSystems, Foster City, Calif.). Size separation of the fluorescently labeled PCR products was done with internal size standards on an ABI/310 Genetic Analyzer capillary electrophoresis instrument (PE Biosystems). GeneScan analysis (including comparison with allelic ladder runs for allelic size designation) was performed, and the peak heights and areas were recorded.

The linear mixture analysis used the mixed DNA profile data d, along with the reference profile genotype a. The LMA heuristic search algorithm was implemented in MATLAB (The MathWorks, Natick, Mass.), and used to analyze the data on a Macintosh PowerBook G3 (Apple Computer, Cupertino, Calif.). The automated heuristic algorithm was applied to each data case, with the program searching for local minima to compute the mixture weight w and the unknown genotype profile b. The computation time for each problem was under 0.1 seconds. The computed profile was compared with the actual profile for individual B. (While known in advance for assessment purposes, neither the mixture weight w nor B's profile were used in the calculations.)

Mixture Deconvolution

Mixture deconvolution was performed on the data, as described above. Five deviation curves are shown in FIG. 6, each plotting squared deviation against the mixture weight. From left to right, these curves correspond to the heuristic functions of the 10:90 (plus), 30:70 (solid), 50:50 (cross), 70:30 (dash), and 90:10 (dot) mixture ratios. The minima of these curves are located near 10%, 30%, 50%, 70%, and 90%, respectively, demonstrating that heuristic minimization infers the proper mixture weight. The shape of the 90:10 (dot) curve reflects the trajectory through allele space as the weight changes from 0 to 1. Note that the minimum has a parabolic shape.

The following expected ratios produced the estimated mixture weights and standard deviations:

| expected | estimated w | estimated $\sigma_w$ |
|---|---|---|
| 10:90 | 11.09% | 1.02% |
| 30:70 | 29.53% | 0.90% |
| 50:50 | 48.43% | 1.12% |
| 70:30 | 69.59% | 0.85% |
| 90:10 | 89.04% | 0.81% |

Note that the standard deviations are relatively small. In every case, the estimated mixture weight is within two standard deviations of the expected ratios.

One hundred alleles were estimated (5 experiments×10 loci per experiment×2 alleles per locus). Due to experimental variation, not all alleles can be called uniquely. However, under the assumption of unique allele calls, there was one incorrect call, for an miscall rate of 1%. The miscall was in the 90:10 experiment at locus D21, where the true heterozygote genotype (2,3) was estimated to be a homozygote genotype (2,2). This was due to the low quantity of b's DNA present in the extreme 90:10 mixture case.

The data d, reference a, and estimated $b(w_0)$ are shown in FIG. 7. The quantitative data d of the 30:70 mixture experiment is shown at every SGMplus locus (first row). Also shown is the known reference profile of individual a (second row). Using mixture deconvolution, the computer estimates the unknown genotype $b(w_0)$ (third row) and the mixture weight $w_0$. Note that the estimated genotype is the same as the true genotype.

Distribution of d

The error vector e is computed from $(1-w_0)[b(w_0)-\hat{b}(w_0)]$, where $w_0$ is the minimizing weight parameter, $b(w_0)$ is the continuous estimate of the genotype parameter, and $\hat{b}(w_0)$ is the integer-valued estimate that is the closest valid genotype to $b(w_0)$. With K=31 alleles, the sample variance $S^2$ is estimated as $$\frac{\|e\|^2}{K-1} \cdot P\{d \mid G, w\} = \frac{1}{(2\pi\hat{\sigma}_d^2)^{\frac{K}{2}}} \exp\left[-\frac{\|G \cdot w - d\|^2}{2\hat{\sigma}_d^2}\right]$$

The estimate of $\sigma_d$ is taken as the square root of the sample variance, with $\hat{\sigma}_d = 0.0407 = \sqrt{0.001658}$.

Once $\sigma_d$ has been estimated, the probability distribution centered at d can be approximated as the multivariate normal:

$$P\{d \mid G, w\} = \frac{1}{(2\pi\hat{\sigma}_d^2)^{\frac{K}{2}}} \exp\left[-\frac{\|G \cdot w - d\|^2}{2\hat{\sigma}_d^2}\right]$$

Here, K=31, and G is the matrix formed from the genotype column vectors a and b.

Distribution of w

The variance of w, $\hat{\sigma}_w^2$, is estimated from $\hat{\sigma}_d^2$ as $\hat{\sigma}_w^2 = \hat{\sigma}_d^2 (G'\cdot G)^{-1}$. For example, in the 70:30 mixture case (with b as the minor component), $$(G' \cdot G) = \begin{bmatrix} 24 & 5 \\ 5 & 24 \end{bmatrix}; (G' \cdot G)^{-1} = \begin{bmatrix} 0.0436 & -0.0091 \\ -0.0091 & 0.0436 \end{bmatrix};$$

$$\sqrt{(G' \cdot G)_{11}^{-1}} = 0.2087$$

and, with $\hat{\sigma}_d = 0.0407$, one computes $$\hat{\sigma}_w = \hat{\sigma}_d \sqrt{(G'\cdot G)_{11}^{-1}}$$

the standard deviation $\hat{\sigma}_w$ for genotype a's weight wA as $$\hat{\sigma}_w = 0.0085 = (0.0407)(0.2087).$$

This calculation is the source of the 0.85% standard deviation value for the 70:30 mixture experiment appearing in the table above.

From the estimated mixture weight (69.59%) and standard deviation (0.85%), one can compute a confidence interval for the 70:30 experiment. With the Z distribution test ($Z_{0.025} = 1.96$), the 95% confidence interval is [67.92%, 71.25%]; using the more exact t distribution test ($t_{0.025} = 2.04$; dof=30), the 95% confidence interval is [67.85%, 71.32%]. These two confidence intervals are essentially equivalent, and both contain the predicted value of 70% with a high p value. Note that mixture deconvolution computes a rather tight estimate on the mixture weight, with 95% of the distribution mass concentrated in under 4% of the range.

Likelihood

It is useful to rank the genotypes according to their likelihood ratio LR, dividing the probability of each candidate genotype by the probability of the highest probability genotype. This can be done for the entire genotype, across all loci, or (by the multiplication of independent data rule) one locus at a time. The first approach is best for comparing two genotypes in the context of all the data. The last "locus-based" approach is useful when trying to understand the data in more depth, seeing if there are equivocal loci that might be problematic, and deciding whether to report more than one genotype at a locus when the LR does not discriminate conclusively.

For the 70:30 mixture data, consider the LR computation at locus THO1. This is representative of typical results on these data. Take the LR for two genotypes as the ratio $LR_{i1}(d)$ of $P\{d|G_i\}$ to the maximal probability $P\{d|G_1\}$. Form the log of the likelihood ratio (or "support") as the logarithm of this ratio, or $$lr_{i1}(d) = \ln\left(\frac{P\{d|G_i\}}{P\{d|G_1\}}\right)$$

Report the computed probabilities and lr (in base 10 logarithm units) for the ranked genotypes for the data at this locus in the table:

| genotype | [011] | [002] | [020] | [101] | [110] | [200] |
|---|---|---|---|---|---|---|
| P{d=$G_i$} | 54.064 | 1.2247e-06 | 7.687e-16 | 1.5844e-18 | 3.3288e-22 | 3.7843e-24 |
| lr$_{i1}$ | 0 | −7.6449 | −16.847 | −19.533 | −23.211 | −25.155 |

The first genotype [0 1 1] is about ten million times more likely than the next closest candidate [0 0 2]. This typical result shows very strong support for the selected genotype at this locus.

In some cases, the data are more equivocal, and the LR support can help in deciding which genotypes are likely, and how to report the results. Recall that the one allele miscall (out of a hundred scores) occurred in the 90:10 mixture experiment, at the D21 locus. The likelihood analysis is shown for this data in the following table:

| genotype | [020] | [011] | [110] | [101] | [002] | [200] |
|---|---|---|---|---|---|---|
| P{d=$G_i$} | 32.432 | 10.583 | 0.36474 | 0.00092291 | 6.9245e-05 | 2.4045e-05 |
| lr$_{i1}$ | 0 | −0.48636 | −1.949 | −4.5458 | −5.6706 | −6.1299 |

The table shows that the first two ranked genotypes have comparable likelihood, and that the third genotype may not be an unreasonable possibility. In the reporting of this mixture, the automation program (or a user) in this ambiguous case would elect to report two (or perhaps three) possible genotypes at this locus. This conclusion, that there is more than one likely genotype, is derived entirely from the data using the likelihoods. It would be most useful to visualize these likelihood relationships. A novel method for visualizing such genotype likelihood is demonstrated next.

Visualizing Likelihood

The likelihood function, as a (minimal) sufficient statistic, partitions the genotype space into regions of constant value. In the case of mixture deconvolution, with J=2, an equivalence class for a particular value may be thought of as a conical surface originating at point a, with its center line extending through d, having an angle from this line determined by the constant likelihood (or probability) value. This picture can be a useful visualization in certain applications. (For arbitrary J, the equivalence class is rooted at the known genotype subspace C($G_{known}$), and forms a hyperplane that is tangent to a sphere around data point d.)

A confidence region can be constructed for genotypes based on the data. The sum of squared error deviations follows a chi square distribution. This $\chi^2$ distribution can be used to examine confidence in the results at one locus, a set of loci, or the entire genotype.

Referring to the automatically computer generated FIG. 4.a, the genotype mixture space for the three allele case at locus THO1 is shown for the 70:30 mixture. This space is a two dimensional simplex embedded in the three dimensional measurement space (for three alleles). The six candidate genotypes occupy positions along the boundary (three at vertices, and three along the edges). The possible expected measurements for a two person mixture are described by the solid line (within the simplex) that connects the two genotype points. The data point d is shown in the interior of the triangular space. A 99% confidence chi square radius is drawn around the data point. Part of the b(w) search space is shown by the dashed line extending from a, through d, to b($w_0$).

In the most preferred embodiment, lines are drawn from a to every candidate genotype $b_i$. Each line represents a possible solution for mixtures of genotypes a and $b_i$. Lines that fall within the interior of the circle (or sphere) have sufficient proximity to the data d to permit a probability value that is within the confidence level. Lines that fall entirely outside the circle (or sphere) are outside the confidence region. In FIG. 4.a, only one line falls within the confidence circle. Thus the genotype (2,3) (at the other end of this line emanating from the known genotype (1,2)) is the only genotype which resides within the 99% confidence region.

In an alternative preferred embodiment, the conical surface (or rays) emanating from point a, and tangent to the confidence circle (or sphere) is drawn. Genotype points residing within the conical boundaries (defined by the penumbra of the point and sphere) lie within the conical genotype confidence region, and those outside may be rejected. In FIG. 4.a, only the genotype (2,3) would fall within this penumbra.

Referring to the automatically generated FIG. 4.b, the genotype mixture space for the three allele case at locus D21 is shown for the 90:10 mixture. Recall that the computer reported a small support difference between the most highly ranked possible genotypes. These close probabilities are usefully visualized in the Figure. Here, genotype a is at point (1,3), the true genotype b is at point (2,3), and the data point d is shown in the interior of this space near a. However, multiple lines fall within the 99% confidence data region. These include lines from (1,3) to genotypes (2,3), (2,2), and (just barely) (1,2). Therefore, it is visually apparent that these genotypes should be included in a 99% confidence reporting of candidate genotypes. Computer visualization of a 95% confidence region shows that only the first two highly ranked genotypes would be reported at that level.

There is a natural three dimensional visualization of the likelihood relationships for the four allele case. Referring to the automatically generated FIG. 5, the 99% $\chi^2$ sphere about the data point d is shown. Of all the lines emanating from a to candidate genotypes $b_i$, only one (the line to genotype (2,4)) intersects the confidence sphere. Hence, only this genotype lies within the conical confidence region (i.e., the penumbra of point a and the data confidence sphere).

These automatically generated computer drawings are highly useful in visually clarifying the likelihood, probability, and confidence relationships between the data and the genotypes. The immediate intuition they provide can replace far more tedious, time consuming, and less effective review of nonvisual presentations.

Random Man Likelihood

One can compute the likelihood ratio of the hypothesis of the prosecution relative to the hypothesis of the defense. A typical formulation entails a "random person" hypothesis by the defence (Evett, I. W. and B. S. Weir, Interpreting DNA Evidence: Statistical Genetics for Forensic Scientists, 1998, Sunderland, Mass.: Sinauer Assoc), incorporated by reference. Suppose that $H_p$ is the prosecution's hypothesis that the stain contains the genotypes of the victim a and the defendant $b_1$, while defence hypothesis $H_d$ is that the stain contains the genotypes of the victim a and a random person. This LR can be written as:

$$LR(d) = \frac{Pr\{d|a, b_1\}}{\sum_{\text{genotype } i} Pr\{d|a, b_i\} \cdot Pr\{b_i\}}$$

where the probability computations have been described above.

Consider the 70:30 mixture data, at the locus THO1. Suppose that each of the three alleles have a population frequency of 10%. Then, computing the LRs as described gives an LR(d) of 50, and an lr(d) of 1.699.

The LR(d) of 50 follows from taking the reciprocal of the genotype frequency of $\sim 2p_2 p_3$, or $2(0.1)(0.1)$ which is 0.02; this reciprocal is 50. It is clear from the lr(d) values that there is essentially only one significant term in the denominator, that of the correct genotype. The current art is focused on the population frequencies, and generally includes all of them in the sum. However, using the LMA invention for LRs, the data probabilities overwhelming suggest only one genotype, essentially removing the improbable ones, and appropriately using properly weighted genotype population frequencies. In the preferred embodiment, the $F_{st}$, inbreeding coefficient is accounted for, and bootstrapping is done to adjust for sampling error.

Without this novel data probability correction, the $H_d$ would have been the more usual sum of genotype frequencies $(0.1+0.1+0.1)^2$, or 0.09, leading to an LR of 11.1 (as 1/0.09). Thus, with the assumed 0.1 allele frequencies, the invention increases the LR at this locus by about a factor of 5.

The THO1 locus contributes 1.699 support units (base 10) to $H_p$, over $H_d$. The sum of support across all ten loci (using the 0.1 allele frequency assumption) is 17.022. Therefore, the genotype b found by the method is about a billion billion times more likely than that of a random person.

Posterior Distribution of b

In Bayesian inference, the prior probability of genotypes is moderated by the likelihood probability of the data to determine the posterior probability of the genotypes. In the preceding statement, odds may be used in place of probabilities. While many priors cannot be used in court, a prior probability of a genotype based on estimated frequency in the population may be reasonable. By providing a (novel) means for computing a mixture likelihood, the invention enables the computation of posterior genotype distributions.

Bootstrap Solutions

Bootstrap resampling methods provide a powerful mechanism for obtaining distributions, variances, confidence regions, and other highly useful statistical values. In particular, the bootstrap can be used to determine the distribution for a (randomized) null hypothesis, along with its mean, standard distribution, and confidence regions. Then, hypothesis testing and ranking can proceed on the data by comparison with this null distribution.

(2 unknowns) In the case with J individuals, with two genotypes unknown, it is possible to effectively match against a database of feasible suspects. This is done using mixture deconvolution, together with bootstrap resampling. Consider the case with J=2. Using the 70:30 mixture data, with B resamplings, in each iteration:

A genotype a* is randomly generated according to specified (e.g., uniform) population allele frequencies, with alleles drawn from the mixture data.

Mixture deconvolution is run on a* and d to estimate b* and w*.

The standard deviations $\sigma_d^*$ and $\sigma_w^*$ are estimated, and recorded.

The bootstrap statistic used here is the standard deviation $\sigma$. This is used as a confidence score for the quality of the fitted least squares solution. While either variance is useful, $\sigma_w$ permits comparison between experiments using an invariant [0,1] scale, independently of the geometry of each solution. On completing the resampling iterations, useful population statistics are computed by the bootstrap plug-in principle, such as the resampled distribution mean and standard deviation.

Referring to FIG. 8.a, the resampled distribution of standard deviations $\sigma_w^*$ is shown for B=1000 iterations, along with the known minimum solution. The distribution has a normal-like central form. The mean is 0.04297, and the standard distribution is 0.00575. The distribution is bracketed with a minimum of Z=−2.64 standard units (SU), and maximum of Z=4.52 SU. The statistic of the correct solution is shown at the left, located Z=−6.00 SUs to the left of the mean.

In the preferred embodiment, individual genotypes from a known genotype are tested as above, but they are drawn from a database of possible suspects (e.g., a DNA database) rather than simulated. The candidate suspects are preferably limited to those that share a sufficient number of alleles with the observed mixture data. The resampled distribution and its statistics show that incorrect genotypes would tend to follow the resampled distribution. However, when a correct genotype is found, it is a clear outlier from the others. In this case, the Z=−6 score of the actual genotype corresponds to a normally distributed probability of one in a billion. Such probability information can be very useful for ranking the candidates. When following up database leads, the ranking makes clear which individual(s) are the outliers, and to what degree.

(1 unknown) In the case of J individuals, with J−1 genotypes $a_j$ known, but one genotype b unknown, it can be useful to assess the quality of the solution in a distribution-free way. This is done comparing the quality of the mixture deconvolution estimate b (i.e., $\sigma_w$) against the quality of randomly resampled genotypes. Consider the case with J=2. Using the 70:30 mixture data, with B resamplings, in each iteration:

A genotype b* is randomly generated according to specified (e.g., uniform) population allele frequencies, with alleles drawn from the mixture data, by either (a) including all these alleles, or (b) removing alleles that are incompatible with a and the data d.

The mixture weight w* is computed by perpendicularly projecting d onto the C(G) space, and taking ratios. This maintains the simplex constraints on w.

The standard deviations $\sigma_d^*$ and $\sigma_w^*$ are estimated, and recorded.

Referring to FIG. 8.b, resampling is shown using the "sampling all alleles" version, since that is most compatible for comparison with the current art. The resampled distribution of standard deviations $\sigma_w^*$ is shown for B=1000 resampling iterations, along with the known minimum solution. The distribution has a normal-like central form. The mean is 0.06623, and the standard distribution is 0.01340. The distribution is bracketed with a minimum of Z=−2.51 SUs, and maximum of Z=4.63 SU. The statistic of the correct solution is shown at the left, located Z=−4.31 SUs to the left of the mean. This corresponds to a probability of one in a hundred thousand, and shows high confidence in the genotype solution G=[a b], relative to other alternatives.

(General likelihood ratios) There are both parametric and nonparametric approaches to bootstrapping the likelihood ratio, as described (Efron, B. and R. J. Tibshirani, An Introduction to the Bootstrap, 1993, New York: Chapman & Hall), incorporated by reference. An LR can be formed to compare any two competing hypotheses, involving any number of known and unknown contributors to a mixture. The question is how much support this LR has in the data. The specific hypothesis pair explored in this data simulation was $$LR(d) = \frac{Pr\{d|H_p\}}{Pr\{d|H_d\}} = \frac{Pr\{d|a, b^*\}}{Pr\{d|c^*, b^*\}}$$

The prosecution hypothesis $H_p$ is that the data contains the genotypes of a known person a and a random person b*, whereas the defence hypothesis $H_d$ is that the data contains the genotypes of the two random people a* and b*. When the genotypes are fully specified, the geometric constraints place w in a relatively small region of the J−1 simplex. Therefore, the minimum distance to the perpendicular error $(I-P_{G^*})d$ is a useful approximation to the (more exact, but more costly) integration over the multidimensional normal distribution considering all w.

Specifically, for any fully specified pair of hypotheses, the support function (log of the likelihood) has the form $$lr_{i1}(d) = \ln\left(\frac{P\{d|H_p\}}{P\{d|H_d\}}\right) \cong \frac{\|G_p^* \cdot w_{0,p} - d\|^2 - \|G_d^* \cdot w_{0,d} - d\|^2}{2\hat{\sigma}_{data}^2}$$

For each simulated hypothesis set, estimate the sum of squares term for a randomly resampled genotype G* by computing the perpendicular projection operator $P_{G^*}$, determining the minimum error vector by a matrix multiplication $e=(I-P_{G^*})d$, and then computing the squared error as the vector product e'e. The lr is calculated as the difference between the squared error terms. After bootstrapping for B iterations, the question is then how far the null difference of 0 lies in standard Z units from the center of the simulated distribution.

Setting B=1000 (preferably, 500≤B≤2000), and using the 70:30 mixture data, known genotype a was set to the major component, and the two unknown genotypes b* and c* were simulated. Using the correct a, a normally shaped distribution was obtained for the bootstrapped difference of squares, with Z about 3.0 (mean of 4.62, standard deviation of 1.52). This shows that the data support an LR that includes individual a in the mixture, as $H_p$ suggested, relative to a random person (i.e., 0 SU), as $H_d$ suggested. (Note that with all random individuals, in other simulations Z=0.0, as expected.)

This approach simulates the random components of any hypothesis set, and uses statistical resampling on the fully specified LR to determine the confidence in the LR or its support. The approach is generally applicable to all $H_p$ and $H_d$ hypothesis sets and their LRs. With simple bootstrapping, it works best (on geometrical grounds) when the specified a (e.g., the suspect) is a major contributor to the mixture. To use the method in its most general form, it is preferable to employ more powerful statistical simulation methods, such as MCMC and empirical Bayes.

Special Analyses (Few loci suffice) It is believed in the current art that many loci are required for mixture analysis, and that the current megaplexes (e.g., 15 loci) are more powerful in mixture resolution than are the smaller panels. However, empirical studies using LMA on laboratory data show that this is not the case. Therefore, smaller (hence less costly, time consuming, and complex) panels may suffice for many forensic applications.

Referring to the 70:30 mixture data d, the major component was used as a known reference sample a, and mixture deconvolution was applied to d and a to estimate the unknown genotype b and the mixing weight $w_0$. In each analysis experiment, a locus order was randomly selected, loci were added one at a time, and, for each partial set of i loci (1≤i≤I, I=10, the number of STR loci), mixture deconvolution was applied to the partial data set. After deconvolution, the quality of the result was assessed by computing the standard deviation $\sigma_w$ as a confidence score. This experiment was repeated many times.

In a typical experiment, the results for cycle i are shown. The columns are (1) the number i of loci in the data subset, (2) the difference of the estimated weight from the final solution ($w_0$=69.586%), and (3) the standard deviation of the estimated weight.

| i | $(w - w_0)\%$ | $\sigma_w\%$ |
|---|---|---|
| 1 | −0.0791 | 1.5854 |
| 2 | 0.8009 | 1.8696 |
| 3 | −2.3509 | 1.2680 |
| 4 | 0.2491 | 1.2455 |
| 5 | −0.7744 | 0.9179 |
| 6 | −0.7696 | 1.0026 |
| 7 | −0.7746 | 1.0314 |
| 8 | −0.2158 | 0.8824 |
| 9 | 0 | 0.8335 |
| 10 | 0 | 0.8499 |

By the fifth cycle, with i=5 loci, the confidence in the weight (i.e., the standard deviation) has converged to about 1%, and then stayed at that level, with final values of about 0.85%. The weight estimate itself has converged to within one percentage point of the final $w_0$ by the fourth cycle. That is, most of the of the information in the mixture has been extracted using just i=5 loci. This reanalysis of the data suggests that very large multiplex panels (e.g., with I>10) may not be essential for mixture analysis in all cases.

In this case, there were 3 four allele cases found in the first five loci. Current manual analysis depends largely on four allele locus data. Does all the resolving power of mixture analysis reside in the four allele data? The next reanalysis shows that this is not the case.

(Three allele data). In the current art, large multiplex STR sets (e.g., roughly 10-20 markers) are preferred for mixture analysis. This is due in large part to the current need for four allele locus data in two person mixture cases when manually analyzing the data. Examiners who elect to use peak quantification data begin with the four allele cases to identify the major and minor contributors, and coarsely estimate the mixture weight (Clayton, T. M., et al., Analysis and interpretation of mixed forensic stains using DNA STR profiling. Forensic Sci. Int., 1998, 91: p. 55-70), incorporated by reference. The human inspection methods that are prevalent in the current art can do little with two or three allele locus data alone, since such data are not clearly resolved by manual analysis. This approach necessitates using large panels (at greater expense and effort) in order to randomly assure the presence of four allele locus data.

Using LMA on real mixture data shows that four allele loci are not required. Referring to the 70:30 mixture data d, the major component was used as a known reference sample a, and mixture deconvolution was applied to d and a to estimate the unknown genotype b and the mixing weight $w_0$. However, only the five loci showing three alleles were retained in the reanalysis.

Mixture deconvolution estimated a mixing weight of 70.50%, with $\sigma_w$=1.18%. That is, the computer found a good solution (less than 1% from the best estimate) with high confidence (a 1% standard deviation) using only five STR loci, all of which had three alleles. The computation time was 35 milliseconds on a Macintosh Cube/G4. In the current art, this analysis would be very difficult (if not impossible) by visual data inspection methods, and the time spent would be measured in hours, not milliseconds.

(Biallelic SNP analysis) Indeed, two alleles per locus are enough to resolve DNA mixtures, using quantitative data and mixture deconvolution analysis. This is demonstrated on single nucleotide polymorphism (SNP) marker simulation data.

Biallelic data was simulated for different size panels of I SNP loci. The simulator generated random biallelic genotypes a and b at each locus. A mixture weight w was set, and the simulated mixture data d was generated as d=G·w+e, where G=[a b], and e is a random noise vector included to model measurement error. Mixture deconvolution was then applied to d and a, with the computer estimating genotype b and mixture weight w. Variances were computed from the linear model, providing estimates of $\sigma_d$ and $\sigma_w$.

A wide range of values for I and w were explored in the experiments. Consider the experiment with I=10 loci, and w=95%. This is an interesting case, since it represents few SNP loci, and an unknown minor contributor weight of just 5%. The results of a typical run's analysis are wA=94.42%, wB=5.58%, and $\sigma_w$=0.98%. That is, the linear analysis finds the correct solution with high confidence.

These results suggest that the design, use, quantitation, and detection of SNP-based assays for DNA mixture analysis should account for the power of LMA as a powerful, fast, and accurate resolution method. Specifically, fewer loci are needed (reduced cost and effort), as long as the data quality, quantification, and analysis are of appropriately high quality.

(Three person analysis) More than J=2 persons can be resolved using LMA. Data were generated by mixing DNA from three individuals in different proportions, amplifying the mixtures using SGMplus, running the products out on an ABI/310 automated DNA sequencer, and then recording the peak quantifications (height, area, size, genotype). The data used in this example were from the (very approximate) 4:1:1 DNA combination, with 44 alleles across the 10 STR loci.

When all three genotypes are known, LMA can directly solve for the actual mixture weights. Including a constraint that the weights must sum to unity, LMA determined the weights as wA=70.56%, wB=11.43%, and wC=18.01%.

Next, suppose that the genotypes a and b are known, but that genotype c (and the mixture weights w) are not known. Applying an initial coarse search (1% spacing) on the 2-D search space, mixture deconvolution estimated the weights as wA=70%, wB=11%, and wC=19%, which agrees with the "all knowns" calculation. This result demonstrates that LMA has application to J>2 contributors.

(Other lab data) The automation methods were applied to data from other laboratories, obtaining accurate results. For example, there was a reanalysis of the original six locus STR data (provided by Dr. Peter Gill) underlying the quantitative analysis of mixture sample MT/NO in (Gill P, Sparkes R, Pinchin R, Clayton T M, Whitaker J P, Buckleton J. Interpreting simple STR mixtures using allele peak area. Forensic Sci. Int. 1998;91:41-53), incorporated by reference. Taking individual MT as the known reference profile, for each approximate mixing ratio (1:10, 1:5, 1:2, 1:1, 2:1, 5:1, 10:1), exact mixture weights were derived and individual NO's genotype was estimated. The respective computed weights (10.02%, 13.83%, 27.87%, 41.89%, 58.43%, 77.25%, 86.66%) are in close agreement with the four allele locus weights that they had estimated (Table 6 for 5 ng DNA in Gill P, Sparkes R, Pinchin R, Clayton T M, Whitaker J P, Buckleton J. Interpreting simple STR mixtures using allele peak area. Forensic Sci. Int. 1998;91:41-53).

Forensic Applications

Identify Individuals

Linear mixture analysis is useful for identifying individuals from mixed stains. This has application, for example, in individual identity, where DNAs (e.g., from people, children, accident victims, crime victims, perpetrators, medical patients, animals, plants, other living things with DNA) may be mixed together into a single mixed sample. Then, mixture deconvolution can resolve the mixed data into its component parts. This can be done with the aid of reference individuals, though it is not required.

A particularly useful aspect of the method is that given data d from a mixed stain, together with one or more reference individuals a, a component individual b can be determined along with the mixture weights w. When the data provide sufficient support, this determination can be essentially unique. Since the method also provides estimates of the error e, estimates of the variances (and standard deviations) $\sigma_d$, $\sigma_w$, and $\sigma_b$, can be computed from the data. These values can be used to estimate probabilities and perform statistical tests. Moreover, they provide a quantitative estimate of the quality of a solution.

Unique identification of individual components of mixed DNA samples is useful for finding suspects from DNA evidence, and for identifying individuals from DNA data in forensic and nonforensic situations. An individual's genotype can be matched against a database for definitive identification. This database might include evidence, victims, suspects, other individuals in relevant cases, law enforcement personnel, or other individuals (e.g., known offenders) who might be possible candidates for matching the genotype. In one preferred embodiment, the database is a state, national or international DNA database of convicted offenders.

When there are no (or only some) reference individuals, but other information (such as a database of profiles of candidate component genotypes) is available, then the invention can similarly derive such genotypes and statistical confidences from the DNA mixture data. This is useful in finding suspect individuals who might be on such a database, and has particular application to finding persons (e.g., criminals, missing persons) who might be on such a database.

When there is little or no supplementary information, the LMA method permits computation of probabilities, and evaluation of hypotheses. For example, a likelihood ratio can compare the likelihood of the data under two different models. Integrating (either directly, or in conjunction with statistical resampling) over the parameters (e.g., mixture weights, contributing genotypes) using the linear model invention enables robust and accurate evaluation of the evidence.

DNA Cryptography

The ability of the invention to uniquely identify individuals from a mixture given reference information enables the encoding and decoding of individual identity by using mixed DNA samples. For example, an individual's DNA could be mixed with the DNA from J−1 other individuals. If J−1 (or J−L, L small) of these individual genotypes were known to a decoder (either directly, or through a database of candidate genotypes), then the individual's genotype could be uniquely determined from the DNA mixture. Moreover, if an insufficient number M (i.e., M zero or M small) of these individuals were known to a decoder, then the problem of resolving J−M individuals from the mixture would be computationally intractable, and the identity of the individual would be masked by the other contributors, and essentially unknowable. This provides a means of communicating in confidence the identity of an individual, or encrypted messages. A large set of secure cryptographic protocols are immediately enabled once this nucleic acid encoding scheme is used (Schneier, B., Applied Cryptography, second ed 1996, New York: John Wiley & Sons), incorporated by reference.

One typical application of DNA cryptography is in sending secure messages. Suppose that a mixed DNA genotype is used as a encryption key. For example, one component of the key identifies the sender, and other component identifies the recipient. (Reference DNAs may be used, instead of, or in addition to, the actual individual's DNA. Additional DNAs can be used to further increase the security of the encryption.) A message encoded with the mixed DNA sample can then be securely sent.

In one preferred embodiment, a message is encoded using an encryption key derived from the sender's genotype. A DNA stain containing DNA from both recipient and sender, is also sent. Third parties cannot resolve the mixture into its components. Both recipient and sender know half the encoding: their own DNA. By supplying their own genotype as a reference, the mixture deconvolution invention instantly provides the recipient with knowledge of the other sender's genotype. The sender's genotype is then used to decode the message. Additional reference genotypes (known to one of the parties) can be used to further increase the security of the mixed DNA encryption key.

The DNA cryptography has application to medical records. In another preferred embodiment, an individual's genotype is used to encode a message. A particularly useful message is medical record information about that individual, which can be encoded using the individual's genotype, and then posted in a public or semiprivate location (e.g., on an Internet database) indexed by this genotype. When medical personnel need to retrieve medical record information on an individual whom they are caring for, by having the person available, they can readily obtain the individual's genotype from blood or other tissue, and thereby decode the individual's medical records. Other public key methods can be devised; these may include additional security codes. Moreover, information other than medical records can be communicated in this way. The knowledge of the STR loci used can constitute another level of encoding and decoding. DNA cryptography has utility in many other cryptographic applications, using a wide variety of cryptographic protocols, which are well-known in the art (Schneier, B., Applied Cryptography, second ed 1996, New York: John Wiley & Sons), incorporated by reference.

Convict Criminals

DNA mixtures are currently analyzed by human inspection of qualitative data (e.g., electrophoretic bands are present, absent, or something in between). Moreover, they are recorded on databases and reported in court in a similarly qualitative way, using descriptors such as "major" or "minor" band, and "the suspect cannot be excluded" from the mixture. Such statements are not optimally compelling in court, and lead to crude database searches generating multiple hits.

Linear mixture analysis of quantitative data changes this situation. Precise and accurate quantitative analysis of the mixture data can reveal unique identities in many cases. Moreover, these mixture analyses can be backed up by statistical certainties that are useful in convincing presentation of evidence. The increased certainty of identification is reflected in the increased likelihood ratios, as well as other probabilities and statistics, as described above.

As discussed, with the random person hypothesis of the defense, current LR analysis gives far too much away to the defense (National Research Council, Evaluation of Forensic DNA Evidence: Update on Evaluating DNA Evidence, 1996, Washington, D.C.: National Academy Press), incorporated by reference. Linear mixture analysis can reduce such inflated LRs by many orders of magnitude. The LR can be improved by using standard bootstrapping techniques on the population frequencies to remove much of the sampling error. It is preferable to consider inbreeding coefficients when computing the prior genotype probabilities from the allele frequencies.

The invention includes using quantitative data. This may entail proper analysis or active preservation of the raw STR data, including the gel or capillary electrophoresis data files. Removing or destroying this highly quantitative information can lead to suboptimal data analysis or lost criminal convictions. The invention enables mathematical estimation of genotypes, together with statistical certainties, that overcome the qualitative limitations of the current art, and can lead to greater certainty in human identification with increased likelihood of conviction in problematic cases.

Generate Reports

Preparing and reviewing reports on mixed DNA samples is tedious and time consuming work for the forensic analyst. This DNA analysis and reporting expertise is also quite expensive, and represents the single greatest cost in crime laboratory DNA analysis. It would be useful to automate this work, including the report generation. This automation has the advantages of higher speed, more rapid turnaround, uniformly high quality, reduced expense, eliminating casework backlogs, alleviating tedium, and objectivity in both analysis and reporting.

The linear mixture analysis and mixture deconvolution methods are designed for computer-based automation of DNA analysis. The results are computed mathematically, and then can be presented automatically as tables and figures via a user interface to the forensic analyst. This analysis and presentation automation provides a mechanism for automated report generation.

There is a basic template for reporting DNA evidence. Within this template, there are information and analyses that are unique to the case, and other information that is generally included. In one preferred embodiment, a template is developed in a document preparation environment (DPE) that provides for references to other files and variables. Preferable formats include readable documents (e.g., word processors, RTF), hypertext (e.g., HTML), and other portable document formats (e.g., PDF). A preferred DPE that can output many different common formats is FRAMEMAKER® document preparation software (Adobe Systems, San Jose, Calif.). A DPE template is a complete document that describes the text and graphics for a standard report, either directly or by reference to variables and files.

After the automated mixture analysis, possibly including human review and editing, the computer generates all variables, text, table, figures, diagrams and other presentation materials related to the DNA analysis, and preserves them in files (named according to an agreed upon convention). The DCE template report document refers to these files, using the agreed upon file naming convention, so that these case-specific materials are included in the appropriate locations in the document. The DCE document preparation program is then run to create a document that includes both the general background and case specific information. This DCE report document, including the case related analysis information (possibly including tables and figures), is then preferably output as a bookmarked PDF file. The resulting PDF case report can be electronically stored and transferred, viewed and searched cross platform on local computers or via a network (LAN or WAN), printed, and rapidly provided (e.g., via email) to a crime laboratory or attorney for use as documented evidence.

Clean up DNA Databases

Many DNA databases permit the inclusion of qualitatively analyzed mixed DNA samples. This is particularly true of the "forensic" or "investigative lead" database components, that contain evidence from unsolved crimes that can be used for matching against DNA profiles.

When these mixed DNA samples are matched against individual or mixed DNA queries, many items (rather than a unique one) can match. Instead of a single DNA query uniquely matching a single DNA database entry, the DNA query can degenerately match a multiplicity of mixed DNA database entries. This degeneracy is only compounded when mixed DNA queries are made. Mixture degeneracy corrupts the database, replacing highly informative unique query matches with large uninformative lists. In these large lists, virtually all the entries are unrelated to the DNA query.

To prevent this database corruption with mixed DNA profiles, it would be useful to clean up the entries prior to their inclusion on the database. When the raw (or other quantitative) STR data are available, this clean up is readily implemented by the mixture deconvolution invention. For example, consider the common case of a two person mixture containing a known victim and an unknown perpetrator. Mixture deconvolution estimates the genotype of the unknown perpetrator, along with a confidence. (Lower confidences may suggest intelligently using degenerate alleles at some loci.) The resolved unknown perpetrator genotypes are then entered into the forensic database, rather than the usual qualitative (e.g., major and minor peak) multiplicity of degenerate alleles. The result is far more uniqueness in subsequent DNA query matches, with an associated increase in the informativeness and utility of the matches.

Clean up DNA Queries

When performing DNA matches against a DNA database, current practice uses mixed DNA stains with degenerate alleles. This practice produces degenerate matches, returning lists of candidate matches, rather than a unique match. Most (if not all) of the entries on this list are typically spurious. The length of these spuriously matching lists grows as the size of the DNA database increases.

With mixture deconvolution, the genotype b of an unknown contributor can often be uniquely recovered from the data d and the victim(s) a, along with statistical confidence measures. Thus, using the resolved mixture b, instead of the qualitative unresolved data d, a unique appropriate database match can be obtained. Moreover, the result of this match is highly useful, since it removes the inherent ambiguity of degenerate database matching, and largely eliminates spurious matches. Even when there is more than one unknown contributor to d, the invention's bootstrap simulation methods permit matching of the mixed data against the database for relatively unique results.

Reduce Investigative Work

Of all the costs in using DNA technology to find criminals, the greatest one is the actual investigative work involved in using the DNA evidence to follow leads. One reason why this cost is so high is the large number of leads generated by degenerate matches. Following one lead is expensive; following dozens can be prohibitive. And as the sizes of the DNA databases increase, the investigative cost of degenerate matches (from mixed crime stains or mixed database entries) will increase further.

The mixture deconvolution invention overcomes this developing bottleneck. By cleaning up the information prior to its use, the database searching results become more unique and less degenerate. This relative uniqueness translates into reduced investigative work, and greatly reduced costs to society for putting DNA technology into practice. The natural business model for mixture deconvolution therefore includes consideration for reducing this investigative burden.

Catch Criminals

The ultimate cost of degenerate DNA matches is losing the ability to use DNA technology to find criminals at all. Too many leads amount to no useful leads, since large numbers of low information leads cannot be practically acted upon due to finite law enforcement resources. Then society pays the highest cost: the criminal is not found, not brought to justice, and continues to commit further crimes. This has a high financial, societal, economic, and human cost, which can be quantified. For example, with sexual assault crimes the estimated dollar cost to the victim and society (when the victim's quality of life is quantified) is $87,000 per case (Victim Costs and Consequences: A New Look, National Institute of Justice Research Report, January 1996), incorporated by reference.

The mixture deconvolution invention can reduce this ultimate cost by cleaning up the DNA mixture samples prior to using the data with a database. This clean up reduces the degeneracy of the DNA matches, increases the information resulting from a database match, and increases the likelihood of catching criminals using DNA technology.

Reduce Laboratory Work

In preparing potentially mixed DNA samples for PCR analysis, crime labs typically attempt to separate different tissues whenever possible. This is done to help avoid analyzing mixture traces, which is difficult, time consuming, and yields uncertain results in the current art.

In sexual assault cases, differential DNA extraction is conducted on semen stains in order to isolate the semen as best as possible. This is done because, a priori, semen stains are considered to be mixed DNA samples, and the best possible (i.e., unmixed) evidence is required for finding and convicting the assailant. Thus, mixture separation is attempted by laboratory separation processes. The full differential extraction protocols for isolating sperm DNA are laborious, time consuming, and expensive. They entail differential cell lysis, and repeatedly performing Proteinase K digestions, centrifugations, organic extractions, and incubations; these steps are followed by purification (e.g., using micro concentration). There are also Chelex-based methods. These procedures consume much (if not most) of the laboratory effort and time (often measured in days) required to for laboratory analysis of the DNA sample. This time factor contributes to the backlog and delay in processing rape kits.

There are also modified differential DNA extraction procedures that are much faster and simpler. These procedures eliminate most of the repetitious Proteinase K digestions, organic solvent separations, and centrifugations, reducing the total extraction effort from days to hours. However, they do not provide the same degree of separation of the sperm DNA template as does the costlier full differential extraction. In fact, highly mixed DNA samples will often result.

With the mixture deconvolution invention, it is feasible to replace days of laboratory separation effort with seconds of automated computer analysis time. The result is the same: the assailant's sperm cells genotype b is separated from the victim's epithelial genotype a using the mixed data d. The invention enables crime labs to use faster, simpler and less expensive DNA extraction methods, with an order of magnitude difference. The computer performs the refined DNA analysis, instead of the lab, resolving the mixture into its component genotypes.

Low Copy Number

Given the power of DNA human identity analysis, forensic scientists are now analyzing ever lower quantities of DNA recovered from crime scenes. Whereas most STR kits work comfortably in the 1 ng range, scientists are now working well below 100 pg, extending down to the 1 pg (several DNA copies) range (Gill, P., et al., An investigation of the rigor of interpretation rules for STRs derived from less than 100 pg of DNA, Forensic Sci Intl, 2000, 112: p. 17-40), incorporated by reference.

To obtain low copy number (LCN) data, laboratories will change the PCR protocol, e.g., increase the cycle number (say, from 28 to 34 cycles with SGMplus). Experiments are often done in duplicate. The combination of less template and more cycles can lead to increased data artifacts. Most prevalent are PCR stutter, allelic dropout, low signal to noise, and mixture contamination.

The automated analysis methods described earlier herein readily remove PCR artifacts such as stutter and relative amplification. To handle allelic dropout, new valid genotypes (e.g., 1 of one allele, and 0 of any another; these do not sum to 2 alleles) must be included in the analysis. For example, in mixture deconvolution, monozygotic genotypes would be added as valid searchable cases. Signal to noise is increased by repeating the experiment, and then combining the results at each locus.

In performing linear mixture analysis, the main effect of noise and dropout are seen in increased error measures (such as variance and standard deviation). While the invention works well on such data, it cannot extract more information from the problem than it actually contains. Therefore, the statistical analysis may suggest multiple genotypes. The variance can be reduced by increasing the informativeness of the data. Techniques for this include experiment repetition, using multiplex panels that contain more loci, and using more informative loci (higher heterozygosity or polymorphism information content (PIC)).

Reduced Panel Size

Current multiplex panels have many STR loci (e.g., from 9 to 15). This provides tremendous discriminating power that can render virtually all of the current and future world's population essentially unique. When matching single profiles to single profiles, the panels (in combination with conventional evidence) provide far more information than what courts actually need for guilt beyond a reasonable doubt.

This panel overdesign is intended to overcome many worst case scenarios. Conventional wisdom holds that:
1. DNA databases will be corrupted with mixture data.
2. DNA evidence will be limited by mixture contamination.
3. Only the four allele cases (in two person mixtures) provide the analyst with useful information for distinguishing the major and minor components.
4. The more loci, the greater the confidence in the evidence.
5. In casework practice, not all loci will provide useful information.

There is certainly truth to these beliefs, based on current practice. However, the mixture analysis invention and its applications moderate these views, somewhat. Specifically:
1. DNA databases need not be highly corrupted by mixture data. Mixture deconvolution can separate out suspect from victim, thereby cleaning up the database.
2. DNA evidence need not be highly corrupted by mixture contamination. Mixture deconvolution can separate out suspect from victim, thereby cleaning up the queries made by crime lab against database.
3. Four allele cases (in two person mixtures) are not needed by the invention's automated computer analysis of mixture data. Indeed, as shown herein, a handful of three allele loci work well for complete resolution.
4. A large number of loci is not needed when using linear mixture analysis. A handful suffice for achieving full confidence, as measured by the variance in the solution.
5. While not all loci may provide useful information, in fact, for mixture resolution, very few are actually needed.

These observations suggest a simpler approach to crime lab stain analysis. Rather than putting considerable effort into obtaining as many loci as possible, it might be preferable to run a smaller panel (with loci that correspond to a database), perform the computer mixture analysis, and determine whether or not a useful identifying genotype has been obtained. If successful, then a crime lab need not expend further resources on additional STR typing. Since the costs of STR panels are priced proportionately to the number of loci, and many samples are analyzed per case, this could lower the incurred cost of information in each case.

Extensions of the Method

Other Markers

The mixture analysis methods work with markers other than STRs. One important class of markers are the single nucleotide repeat polymorphisms (SNPs). In these assays, each component biallelic marker has just two alleles: one of two bases that terminate the reaction.

With minisequencing protocols, SNPs are detected by primer extension of one nucleotide that is a labeled ddNTP terminator. One allele has its base identified with a complementary terminator labeled in a first color (say, blue), while the second allele has its (different) base identified with a complementary terminator labeled in a second color (say, red). Clearly, up to four alleles (one color for each possible nucleic acid base) can be accommodated in this way.

Suppose that after PCR (in the linear range), primer extension is performed on the PCR product with the two differently colored ddNTPs. Consider a single marker having two alleles. A homozygote for the blue allele would produce two blue units and no red units, a homozygote for the red allele would produce two red units and no blue unit, and a heterozygote would produce one blue unit and one red. Thus, the possible genotypes at this locus can be written as $\{[2\ 0], [1\ 1], [0\ 2]\}$, where the first vector element describes the blue allele, and the second one the red allele. This case is isomorphic to the two allele STR situation.

A mixture of J individuals would produce a continuous-valued signal that would be a linear combination of the pure genotypes, according to their DNA template proportion, with the simplex constraint that the sum of the (nonnegative) weight values totaled to unity. Suppose there are I SNP loci, J DNA contributors to the mixture, and K alleles present. Note that K=2I in the biallelic case (and K≤4I when more than two alleles per locus are permitted), with one entry for each detected color. Then one obtains the linear mixture analysis model:

$$d = G \cdot w + e,$$

where d is the observed K×1 data vector, G is K×J matrix of genotype column vectors, w is the J×1 mixture weight vector, and e is the error. With multiple experiments, d becomes a matrix (not a vector) of observations, and the equation changes accordingly.

The mixture deconvolution invention is therefore quite applicable to SNP data. This is because the mathematical form of the problem, and the linear nature of the data, are identical to the problem solved above for any linear mixture model, as illustrated in depth for STRs.

SNP assays can be done by gel or capillary electrophoresis (which permits highly multiplexed one dimensional analysis), and by DNA arrays (which can pack a large number of zero dimensional experiments into a two dimensional format) such as microwell titre plates, and DNA chips or other surface-based DNA comparison technologies. They are attractive for human (and other species) identification because a large amount of data can be obtained at a relatively lower cost per unit of information. This was demonstrated in the data simulations described above.

The mixture analysis methods described will work with any marker system, as long as the detected allele signals vary linearly (or in a similarly monotonically predictable way) with the amount of DNA template that is effectively present. This is because once the linearity condition is met, the data from one or more markers from two or more DNA contributors can linearly modeled as:

$$d = G \cdot w + e,$$

which is a mixture problem that the invention completely solves.

Achieving this linearity condition may require adapting the experiment to the linear analysis method. For example, some molecular biologists prefer to bias their experiments to achieve an all-or-none response, e.g., by saturating the system somehow (say, by using a very large number of PCR cycles). The linear adaptation in this case would entail moving the system away from the saturating parameters, into a linearly (or monotonically) behaving range (say, by reducing the number of PCR cycles).

Other Genotypes

There are valid genotypes other than those used in the above embodiments. One case involves extra alleles (i.e., more than two at a locus). For example, if trisomy 21 is a likely event, then the valid genotypes of a single individual can be extended to handle the three expected chromosomes. This is done by adding to the valid genotype set all possible combinations for the observed alleles that sum to three. With two alleles, for example, the original set $$\{[2\ 0], [1\ 1], [0\ 2]\}$$

is expanded to $$\{[2\ 0], [1\ 1], [0\ 2], [3\ 0], [1\ 2], [2\ 1], [3\ 0]\},$$

which then accommodates the feasible two and three chromosome cases.

Another case involves missing alleles. With LCN applications, allele dropout may occur due to the observable amplification of only one chromosome. If this is expected, then simply augment the valid genotype set with the possibilities of alleles that sum to one. With two alleles, for example, the original set $$\{[2\ 0], [1\ 1], [0\ 2]\}$$

is expanded to $$\{[2\ 0], [1\ 1], [0\ 2], [1\ 0], [0\ 1]\},$$

which then accommodates both feasible one and two chromosome cases.

Other Formats

The invention is not dependent on any particular arrangement of the experimental data. In the DNA amplification, same DNA template is used throughout. For efficiency and consistency of the amplification conditions, a multiplex reaction is preferred. There is no requirement on the specific label or detector used. It is preferred that the experiment be conducted in the linear range of the DNA analysis system.

There is no restriction on the dimensionality of the laboratory system. It can accommodate dimensions of zero (tubes, wells, dots), one (gels, capillaries, mass spectrometry), two (gels, arrays, DNA chips), or higher. There is no restriction on the markers or the marker assay used. The only requirement is that $$d = G \cdot w + e,$$

can be made to be a reasonable model of the system's behavior. For then, the mixture weight can become a constraint on the data that leads to rapid, robust and accurate solutions.

General Solution

The general solution for I markers, J individuals, and K alleles was given above. With 0 unknowns, the mixture weight w can be determined by least squares minimization. With 1 unknown genotype, the missing genotype b can also be determined using mixture deconvolution. With 2 unknown genotypes, the missing genotypes $b_1$ and $b_2$ can be also determined using mixture deconvolution together with bootstrap resampling simulation. With more than 2 unknown genotypes, additional search on the genotype solution space is required, but can be solved with brute force computation, integer programming, or computational geometry minimization techniques. Thus the linear mixture analysis provides a general solution framework for effectively solving any DNA mixture search problem, and providing statistical estimates of the quality of the solution.

With any number of unknowns, bootstrap simulation techniques based on the linear mixture analysis method permit the computation of a null distribution. Any genotype configuration can be statistically assessed against this null distribution. For example, suppose the hypothesis is that J particular individuals are the contributors to a particular mixture d. Then, least squares projection into the J−1 simplex finds the weight parameter solution having the best confidence score. This optimal score can be compared against the sampled null distribution to assess the validity of the hypothesis. Alternatively, the minimal solution can be used to estimate variance in probability calculations, or other statistics (e.g., the sample variance $S^2$) for use in statistical tests (e.g., $\chi^2$ or F). Thus, the linear mixture analysis invention provides a general solution framework for effectively evaluating any DNA mixture hypothesis, and providing useful statistical estimates.

Three Person Mixture

The most preferred embodiment for solving a three person mixture (J=3) with one unknown genotype was described above (i.e., simplex search for error minimization). An alternative embodiment for resolving such a case comprised of one woman and two men is described here using Y-chromosome markers. It entails two data sets and two one dimensional optimizations, instead of the most preferred one data set with one two dimensional optimization.

For known female victim a, and the two male components $b_1$ and $b_2$, write:

$$d = \alpha a + (1-\alpha)[\beta b_1 + (1-\beta)b_2] + e$$

Using Y-chromosome markers, such as (Y-PLEX 6, ReliaGene, New Orleans, La.), type the mixture, obtaining data on the two male components. Use mixture deconvolution on this Y-chromosome data to determine the mixture weight $\beta_0$ between them.

Now write the genotype estimate function for $b_2$ as:

$$b_2(\alpha) = \frac{1}{1-\beta_0}\left[a + \frac{d-a}{1-\alpha} - \beta_0 b_1\right]$$

and the error vector as $$e(\alpha) = (1-\alpha)(1-\beta_0)[b_2(\alpha) - \hat{b}_2]$$

where $\hat{b}_2$ is the closest valid genotype to $b_2(\alpha)$. Use the mixture deconvolution algorithm to minimize $|e|^2$, and to find $b_2$ and $\alpha_0$.

Additional Data

In forensic casework, it is often possible to perform only a single PCR amplification on a sample, due to limited DNA material. However, in many cases the PCR can be repeated. In some circumstances, particularly when the initial mixture deconvolution suggests a high variance or low confidence in a unique solution, it is useful to repeat the experiment (possibly multiple times) to obtain additional data.

In the linear system $d = G \cdot w + e$, d, w and e are column vectors. With repeated experiments, one can write instead the matrix relationships $$D = G \cdot W + E$$

This can confer several advantages:

The additional data permits more accurate estimation of the variances.

The search algorithm can be adjusted to force all columns of W to be equal, so that a common mixing weight in the template is assumed. If this is done, then it is best to amplify all replicates from the same DNA template.

Mixture deconvolution may provide more accurate solutions, particularly when the data are problematic.

Multiple experiments permit the calculation of sample covariances across the alleles. This can reveal correlations between allelic quantities within (or between) loci.

The covariance matrix V can be computed, and used in the modeling of the data. As described above, V appears in the weight variance estimation, the probability distributions, and thus the likelihood calculations.

Experiment repetition is most helpful in certain applications, such as low copy number DNA analysis.

PCR Artifacts

In the most preferred embodiment, PCR artifacts are removed (or attenuated) mathematically by calibrations such "stutter deconvolution" (Martens, H. and T. Naes, Multivariate Calibration 1992, New York: John Wiley & Sons 438; Perlin, M. W., G. Lancia, and S.-K. Ng, Toward fully automated genotyping: genotyping microsatellite markers by deconvolution, Am. J. Hum. Genet., 1995, 57(5): p. 1199-1210), incorporated by reference. The mixture analysis is preferably done after such signal preprocessing. Advantages include a reduction in the dimensionality of the search space, and the use of an integer lattice for search algorithms.

In an alternative embodiment, stutter is not removed prior to mixture deconvolution or LMA. In that case, the dimensionality of the data space is increased by the additional alleles formed by artifactual stutter bands. In such analyses, it is best to include stutter data in the representation of all genotypes, including reference and target genotypes. This will move the genotypes off the integer lattice, and into the quantitative allele measurement space. The effect is that genotype matrix G can assume continuous (rather than purely discrete) values. By the linearity of the stutter transformation, the mixture model and deconvolution will still work well. However, this embodiment has a more complex representation than using the stutter calibrated data.

In an alternative embodiment, relative amplification is not adjusted for prior to mixture deconvolution or LMA. In that case, heterozygotes are better represented by points that are not on the integer lattice, but instead fall along the line between the pure homozygotes at a position based on their relative amplification. This can put continuous (rather than discrete) valued entries in the genotype matrix G. The methods described will operate well in this alternative, if more complex, representation.

Nonforensic Applications

Linear modeling, regression and mixture analysis are well established in the prior art (Christensen, R., Plane Answers to Complex Questions: A Theory of Linear Models, 1996, New York: Springer-Verlag; Martens, H. and T. Naes, Multivariate Calibration, 1992, New York: John Wiley & Sons. 438; Seber, G. A. F., Linear Regression Analysis, 1977, New York: John Wiley & Sons), incorporated by reference. However, the mixture deconvolution methods (for the J−1 knowns case) are novel. They use integer constraints on the genotype to determine a column in the design matrix G by a global minimization. Moreover, the bootstrap simulation methods (for the J−2 knowns case) are novel. They use integer constraints on the genotype, together with an information source (e.g., a database of candidate genotypes), to determine two columns in the design matrix G by multiple global minimizations.

These novel and nonobvious optimization methods have utility in the analysis of data formed by linear combinations and other transformations of discrete data. Initial preprocessing inverts the other transformations, leaving a mixture deconvolution problem. This is solved using the methods described above.

One nonforensic application is cryptography. Consider some binary string (e.g., ASCII) representation T of some text or other discretizable information having length K. Next, consider another discrete string U, also of length (at least) K. (In alternative embodiments, more than one such U are used.) Such U's of arbitrary length are readily available, given the amount of on-line content accessible on the Internet. Each element of T and U is comprised of a 0 or a 1. Choose a weight w (between 0 and 1), and form V as the continuous mixing of T and U, defined by $$V(k) = wT(k) + (1-w)U(k).$$

Round the values V(k) to several decimal places, and introduce additional noise, if desired. That is:

$$V = [T\ U]w + e.$$

Each V(k) element can be represented numerically in at most 8 bits as a byte character, providing natural round-off error.

The vector V has entries that assume values between 0 and 1. The message T is entirely unknowable from V alone. Yet, by having U in hand, mixture deconvolution can instantly recover the information T. In this way, the function $$f(X) = [X\ U]w + e$$

serves as a trapdoor one-way function, for random w and e. It is easy to compute in one direction, and hard to compute in the other. However, given the secret information U, it becomes easy to compute X. Such trapdoor one-way functions are at the heart of modern cryptography (Schneier, B., Applied Cryptography, second ed, 1996, New York: John Wiley & Sons), incorporated by reference. So the methods described herein clearly have utility that goes well beyond forensics and personal identification.

Medicine and Agriculture

There are many settings in biology, medicine, and agriculture where mixed DNA (or RNA) samples occur. These samples can be mixed intentionally, or unintentionally, but the problem remains of determining one or more genotype components.

In biology, mixtures of DNA sequences occur. For example, when sequencing DNA, it is useful to first sequence the two chromosome sample and then somehow determine the component DNA sequences, rather than subclone to first separate and then sequence them. As described in the preceding cryptography example, LMA can deconvolve mixed sequences of discrete information, such as DNA sequences. In HLA typing, for example, the known combinations of sequences permit quantitative information to be resolved using mixture deconvolution.

In medicine, cancer cells are a naturally occurring form of DNA mixtures. In tumors that exhibit microsatellite instability (e.g., from increased STR mutation) or loss of heterozygosity (e.g., from chromosomal alterations), a different typable DNA (the tumor) is mixed in with the normal tissue. By determining the precise amount of the individual's normal DNA, versus the amount of any other DNA (e.g., a diverse tumor population), cancer patients can be diagnosed and monitored using mixture deconvolution. This is done by using the many alleles possibly present at a locus. With diverse tumor tissue subtypes, there may be many alleles present. Quantitative data are collected for d, the individual's known alleles are then used as reference a, and the pattern of the tumor contribution b is determined, along with the mixture weight w and the standard deviation.

In agriculture, animal materials can be mixed, e.g., in food, plant or livestock products. LMA can resolve the mixed samples into their individual components.

Business Model

There are many situations in which automated linear mixture analysis confers economic and other benefits to the user community. At each of these, the natural model is a usage-based fee that reflects a reasonable percentage of the value-added provided. This business model of providing DNA mixture data analysis is novel, and not obvious. It is reasonable and useful because the technology delivers clear benefits and enabling functionalities that cannot be done in any other way in the current art.

In a first preferred embodiment, crime or service laboratories generate their own data from DNA samples. The data quantitation and mixture analysis is then done at their site, or, preferably (from a quality control standpoint) at a separate data service center (DSC). This DSC can be operated by a private for-profit entity, or by a centralized government agency. The case is analyzed, and a report then generated (in whole or part) using the software. The report is provided to the originating laboratory. Usage fees are applied on a per case basis, with surcharges for additional work. The DSC may provide quality assurance services for provider laboratories to ensure that the data is analyzable by quantitative methods.

In a second preferred embodiment, the DSC generates the data, and analyzes it as well. This has the advantage of ensured quality control on the data generation. This can be important when the objective is quantitative data that reflects the output of properly executed data generation. After data analysis, the customer receives the report, and is billed for the case.

There are several feasible customers for database work. When entering mixed samples onto a database, it is the database curators and owners (e.g., a centralized government related entity) that is most concerned about the quality of the entered data for future long-term forensic use. This suggests a usage-based contract with said entity for cleaning up the data. A value added by the invention is the capability of finding criminals at a lower cost.

When analyzing a mixed DNA sample, law enforcement agencies (e.g., prosecutors, police, crime labs) may be interested in identifying genotypes in the mixed sample which are unknown, preferably to match them against a database of possible suspects. In this case, a value added by the invention is the reduced cost, time, and effort of mixture analysis and report generation. There is additional value added in obtaining a higher quality result that can more effectively serve the law enforcement needs of the agency.

When matching against a DNA database, a single correct match will lead to minimal and successful investigative work by the police or other parties. Having a multiplicity of largely incorrect matches creates far greater work, for far less benefit. That is the current art. The invention can (in many cases) reduce this work by over an order of magnitude. The value added in this case is the savings in cost and time in the pursuit of justice.

When using mixed DNA evidence in court, the goal is to obtain a conviction or exoneration, depending on the evidence. The current art produces imprecise, qualitative results that are ill-suited to this purpose. Current assessments often vastly understate the true weight of the evidence. The value added in this situation is the capability of the technology to convict the guilty (and keep them off the street) and to exonerate the innocent (and return them to society). The financial model in this case preferably accounts for the benefit to society of appropriately reduced crime and increased productivity.

System

The LMA invention includes a system for resolving a DNA mixture comprising: (a) means for amplifying a DNA mixture, said means producing amplified products; (b) means for detecting the amplified products, said means in communication with the amplified products, and producing signals; (c) means for quantifying the signals that includes a computing device with memory, said means in communication with the signals, and producing DNA length and concentration estimates; and (d) means for automatically resolving a DNA mixture into one or more component genotypes, said means in communication with the estimates.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method of analyzing a DNA mixture comprised of the steps:
 (a) obtaining a DNA mixture that contains genetic material from at least two contributing individuals;
 (b) amplifying the DNA mixture in a DNA amplification process to produce an amplification product comprising DNA fragments;

(c) producing from the amplification product a signal comprising signal peaks from the DNA fragments;

(d) detecting signal peak amounts in the signal, and quantifying the amounts to produce DNA lengths and concentrations from the mixture to form quantitative genotyping data;

(e) assuming a genotype value of alleles for a contributor to the quantitative genotyping data at a genetic locus;

(f) setting a mixture weight value for a relative proportion of the contributors to the quantitative genotyping data;

(g) forming a linear combination of the genotype values based on the mixture weight value;

(h) deriving with a computer a data variance of the amplification process from a model that includes both the quantitative genotyping data and the linear combination;

(i) determining with the computer a probability of the quantitative genotyping data corresponding to a set of suspects from the DNA mixture at the locus using both the linear combination and the data variance value; (j) computing a probability of a genotype for one of the contributing individuals using the determined probability of the quantitative genotyping data; and (k) comparing the genotype probability with a set of suspect genotypes to identify a likely suspect.

2. The method as described in claim 1 wherein the amplifying step at a locus generates relative amounts of DNA fragments that are proportional to relative amounts of DNA template present in the DNA mixture.

3. The method as described in claim 2 wherein the detecting step generates relative amounts of signal that are proportional to the relative amounts of DNA fragments.

4. The method as described in claim 1 wherein the forming step includes a mathematical operation based on a linear model that relates the quantitative genotyping data to a product of a genotype matrix multiplied by a weight vector that describes the relative contribution of each individual that is considered in the DNA mixture.

5. The method as described in claim 4 wherein after the determining step there is the step of using a computing device to generate a visualization that shows the genotype matrix and the weight vector.

6. The method as described in claim 4 wherein the forming step includes iteratively determining the genotype matrix based on the weight vector, and the weight vector based on the genotype matrix.

7. The method as described in claim 4 wherein the genotype matrix contains entries that are not integer values.

8. The method as described in claim 7 wherein the noninteger values represent an efficiency of the amplification.

9. The method as described in claim 4 wherein the mathematical operation computes a genotype of an individual by subtracting from the data genotypes of other individuals in the mixture in proportion to the weight vector.

10. The method as described in claim 4 wherein the genotype matrix is a design matrix of the linear model.

11. The method as described in claim 4 wherein the weight vector is a regression parameter of the linear model.

12. The method as described in claim 4 wherein the data variance is a parameter of the linear model.

13. The method as described in claim 4 wherein the linear combination of genotypes is represented in a linear model.

14. The method as described in claim 1 wherein the computing step includes determining a probability of each genotype in a set of genotypes of an individual whose DNA is in the DNA mixture.

15. The method as described in claim 1 wherein the computing step includes determining a relative weight of an individual's DNA in the DNA mixture.

16. The method as described in claim 1 wherein the computing step includes determining a statistical confidence in the genotype of the DNA mixture.

17. The method as described in claim 1 wherein the computing step includes recording a genotype likelihood or probability of an individual in a report.

18. The method as described in claim 1 wherein the set of suspect genotypes contains a genotype of a convicted offender individual.

19. The method as described in claim 1 wherein the determining step can process at least one DNA mixture per hour.

20. The method as described in claim 1 wherein the determining step can determine a genotype using a computing device with memory.

21. The method as described in claim 20 in performing the determining step does not exceed one hour.

22. The method as described in claim 20 wherein the determining step is performed entirely by computer, without any human intervention during the determining step.

23. The method as described in claim 1 wherein the amplification includes a single nucleotide polymorphism (SNP) marker.

24. The method as described in claim 1 wherein the analysis includes more than one DNA experiment.

25. The method as described in claim 1 wherein the DNA mixture contains genetic material from more than two individuals.

26. The method as described in claim 1 wherein the assuming step includes a candidate genotype selected from a database of previously determined genotypes.

27. The method as described in claim 26 wherein the determining step produces a set of ranked genotypes that are in the database and match the data.

28. The method as described in claim 1 wherein the amplifying step includes a low copy number PCR protocol.

29. The method as described in claim 1 wherein the data variance model in the deriving step includes an inverse chi square probability distribution.

30. The method as described in claim 1 wherein the probability of the quantitative genotyping data in the determining step is a multivariate normal distribution.

31. The method as described in claim 1 wherein the probability of the quantitative genotyping data is combined with a genotype prior distribution to form a posterior genotype probability distribution.

32. The method as described in claim 31 wherein the prior distribution is computed from population allele frequency information.

33. The method as described in claim 31 wherein the prior distribution is uniformly distributed.

34. A method as described in claim 1, where the quantitative genotyping data obtained in Step (d) is from a short tandem repeat (STR) locus.

35. A method as described in claim 1, where the quantitative genotyping data obtained in Step (d) is from a Y chromosome short tandem repeat (Y-STR) locus.

36. A method as described in claim 1, where the quantitative genotyping data obtained in Step (d) is low copy.

37. A method as described in claim 1, where the quantitative genotyping data obtained in Step (d) is derived from allele peak height or area.

38. A method as described in claim 1, where the quantitative genotyping data obtained in Step (d) is derived from repeated experiments.

39. A method as described in claim 1, where the quantitative genotyping data obtained in Step (d) entails fewer loci.

40. A method as described in claim 1, where the genotype value assumed in Step (e) has an allele count that is continuous, rather than discrete.

41. A method as described in claim 1, where the genotype value assumed in Step (e) accounts for allele dropout.

42. A method as described in claim 1, where the genotype value assumed in Step (e) includes a representation of PCR stutter.

43. A method as described in claim 1, where the genotype value assumed in Step (e) includes a representation of relative amplification.

44. A method as described in claim 1, where the mixture weight value set in Step (f) is related to a mixture weight probability distribution.

45. A method as described in claim 1, where the linear combination formed in Step (g) contains one genotype.

46. A method as described in claim 1, where the linear combination formed in Step (g) contains two genotypes.

47. A method as described in claim 1, where the linear combination formed in Step (g) contains three genotypes.

48. A method as described in claim 1, where the linear combination formed in Step (g) contains more than three genotypes.

49. A method as described in claim 1, where the data variance value derived in Step (h) is conditioned on a genotype value.

50. A method as described in claim 1, where the data variance value derived in Step (h) is a data covariance matrix.

51. A method as described in claim 1, where the data variance value derived in Step (h) is obtained from a calibration.

52. A method as described in claim 1, where the data variance value derived in Step (h) is related to a data variance probability distribution.

53. A method as described in claim 1, where the data variance value derived in Step (h) scales with peak height or area.

54. A method as described in claim 1, where the probability of the quantitative genotyping data determined in Step (i) involves a simulated genotype.

55. A method as described in claim 1, where the probability of the quantitative genotyping data determined in Step (i) uses a function with continuous, rather than binary, values.

56. A method as described in claim 1, where the probability of the quantitative genotyping data determined in Step (i) includes a hierarchical Bayesian model.

57. A method as described in claim 1, where the probability of the quantitative genotyping data determined in Step (i) uses Markov chain Monte Carlo methods.

58. A method as described in claim 1, where a computer draws a visualization of the computed genotype probability.

59. A method as described in claim 1, where genotypes are ranked in the order of their computed probability values.

60. A method as described in claim 1, where DNA mixture data is separated into component genotypes having computed probability.

61. A method as described in claim 1, where a computer generates a genotype report from the computed probability that includes a figure or a table.

62. A method as described in claim 1, where computed genotype probabilities are stored on a DNA database.

63. A method as described in claim 1, where separated genotypes of contributors to a mixture are stored on a DNA database, along with their computed probability.

64. A method as described in claim 1, where the computed genotype probabilities provide more specific investigative leads.

65. A method as described in claim 1, where a service center computes the genotype probabilities from the quantitative genotyping data.

66. A method of analyzing a DNA mixture comprised of the steps:
    (a) obtaining a DNA mixture that contains genetic material from at least two contributing individuals;
    (b) amplifying the DNA mixture in a DNA amplification process to produce an amplification product comprising DNA fragments;
    (c) producing from the amplification product a signal comprising signal peaks from the DNA fragments;
    (d) detecting signal peak amounts in the signal, and quantifying the amounts to produce DNA lengths and concentrations from the mixture to form quantitative genotyping data;
    (e) assuming a genotype value of alleles for a contributor to the quantitative genotyping data at a genetic locus;
    (f) setting a mixture weight value for a relative proportion of the contributors to the quantitative genotyping data;
    (g) forming a linear combination of the genotype values based on the mixture weight value;
    (h) deriving with a computer a data variance of the amplification process from a model that includes both the quantitative genotyping data and the linear combination;
    (i) determining with the computer a probability of the quantitative genotyping corresponding to a set of suspects data from the DNA mixture at the locus using both the linear combination and the data variance value;
    (j) calculating a likelihood ratio of a hypothesis using the determined probability of the quantitative genotyping data; and
    (k) comparing with a set of suspect genotypes using the likelihood ratio to identify a likely suspect.

67. A method as described in claim 66, where the likelihood ratio is calculated from a plurality of genetic loci.

68. A method as described in claim 66, where the likelihood ratio hypothesis is related to identifying an individual.

69. A method as described in claim 66, where the likelihood ratio is calculated on genotypes on a DNA database to find genotype association strength.

70. A method as described in claim 66, where the calculated likelihood ratio provides greater certainty in human identification.

* * * * *